US012103918B2

(12) United States Patent
Weingarten et al.

(10) Patent No.: US 12,103,918 B2
(45) Date of Patent: *Oct. 1, 2024

(54) SYNTHESIS OF CHROMANOL DERIVATIVES

(71) Applicant: BASF SE, Ludwigshafen am Rhein (DE)

(72) Inventors: Melanie Weingarten, Ludwigshafen am Rhein (DE); Wolfgang Siegel, Ludwigshafen am Rhein (DE); Michael Puhl, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 698 days.

This patent is subject to a terminal disclaimer.

(21) Appl. No.: 17/268,981

(22) PCT Filed: Aug. 16, 2019

(86) PCT No.: PCT/EP2019/072029
§ 371 (c)(1),
(2) Date: Feb. 17, 2021

(87) PCT Pub. No.: WO2020/035600
PCT Pub. Date: Feb. 20, 2020

(65) Prior Publication Data
US 2021/0309626 A1  Oct. 7, 2021

(30) Foreign Application Priority Data
Aug. 17, 2018 (EP) ..................................... 18189589

(51) Int. Cl.
*C07D 311/58* (2006.01)
*B01J 21/16* (2006.01)
*B01J 37/06* (2006.01)

(52) U.S. Cl.
CPC ............. *C07D 311/58* (2013.01); *B01J 21/16* (2013.01); *B01J 37/06* (2013.01)

(58) Field of Classification Search
CPC .................................................. C07D 311/58
USPC ....................................................... 549/411
See application file for complete search history.

(56) References Cited

U.S. PATENT DOCUMENTS

| | | | |
|---|---|---|---|
| 2,229,573 A | 1/1941 | Fritz | |
| 4,769,500 A | 9/1988 | Yui et al. | |
| 5,610,113 A | 3/1997 | Matsui et al. | |
| 6,452,023 B1 | 9/2002 | Aquino et al. | |
| 11,673,874 B2 * | 6/2023 | Weingarten | C07D 311/72 549/411 |
| 2005/0171362 A1 | 8/2005 | Bonrath et al. | |
| 2013/0211080 A1 | 8/2013 | Bonrath et al. | |
| 2021/0171489 A1 * | 6/2021 | Weingarten | B01J 37/06 |
| 2021/0309627 A1 * | 10/2021 | Weingarten | C07D 311/72 |

FOREIGN PATENT DOCUMENTS

| | | |
|---|---|---|
| CN | 1890200 A | 1/2007 |
| CN | 103080084 A | 5/2013 |
| DE | 2404621 A1 | 8/1975 |
| DE | 10245198 A1 | 4/2004 |
| EP | 0264823 A1 | 4/1988 |
| EP | 0398636 A1 | 11/1990 |
| EP | 0677520 A1 | 10/1995 |
| EP | 0970953 A1 | 1/2000 |
| JP | 63-101340 A | 5/1988 |
| JP | 07-330754 A | 12/1995 |
| JP | 2000-044556 A | 2/2000 |
| JP | 2007-513121 A | 5/2007 |
| WO | 97/28151 A1 | 8/1997 |
| WO | 2005/054223 A2 | 6/2005 |
| WO | 2012/025587 A1 | 3/2012 |
| WO | 2014/023846 A1 | 2/2014 |

OTHER PUBLICATIONS

Bello Forero et al.: "Propylene Carbonate in Organic Synthesis: Exploring its Potential as a Green Solvent", Current Organic Synthesis vol. 13, No. 6, Oct. 31, 2016 (Oct. 31, 2016), pp. 834-846.
International Preliminary Report on Patentability received for PCT Patent Application No. PCT/EP2019/072029, dated Mar. 4, 2021, 7 pages.
International Search Report and Written Opinion received for PCT Patent Application No. PCT/EP2019/072029, dated Sep. 20, 2019, 9 pages.
Eggersdorfer et al., "One Hundred Years of Vitamins—A Success Story of the Natural Sciences", Angewandte Reviews Int. Ed., vol. 51, 2012, pp. 12960-12990.
Matsui et al., "Metal Ion-Exchanged Montmorillonites as Practical and Useful Solid Catalysts for the Synthesis of Alpha-Tocopherol", Bull. Chem. Soc. Jpn., vol. 69, 1996, pp. 137-139.
Netscher, "Synthesis of Vitamin E", Vitamins and Hormons, vol. 76, 2007, pp. 155-202.
Odinokov et al., "Synthesis of Alpha-tocopherol (vitamin E), vitamin K1-chromanol, and their analogs in the presence of aluminosilicate catalysts Tseokar-10 and Pentasil", Arkivoc, 2003, pp. 101-118.
Scegolev et al., "Mit dem Orden des roten Banners der Arbeit ausgezeichnetes Moskauer Institut für Feinchemietechnik M. W. Lomonossow", UDK: 547.814.I.07 1982, VINITI 7.09.82, No. 4780-82, 1982, 12 pages.
Schaffner et al., "Organic Carbonates as Solvents in Synthesis and Catalysis", Chem. Rev., vol. 110, No. 8, 2010, pp. 4554-4581.

(Continued)

*Primary Examiner* — Niloofar Rahmani

(74) *Attorney, Agent, or Firm* — Faegre Drinker Biddle & Reath LLP

(57) ABSTRACT

The present invention relates to a process for the production of chromanol derivatives, more specifically to a process for preparing a compound of the general formula (I) wherein $R^1$, $R^2$ and $R^3$ independently of each other are selected from hydrogen and methyl, $R^4$ is selected from hydrogen and $C_1$-$C_6$-alkanoyl, and X is selected from $C_1$-$C_{20}$-alkyl and $C_2$-$C_{20}$-alkenyl.

18 Claims, No Drawings

(56) References Cited

OTHER PUBLICATIONS

Tachibana, "Preparation of Vitamin E Using Cation Exchange Resin Complexes of Metal Ions", Bulletin of the Chemical Society of Japan, vol. 50, No. 9, 1977, pp. 2477-2478.
Schager et al., "Synthesis of D,L-a-Tocopherol Using Strong Solid Acids as Catalysts", Journal of Catalysis, vol. 182, Issue 1, Feb. 15, 1999, pp. 282-284.

* cited by examiner

SYNTHESIS OF CHROMANOL DERIVATIVES

CROSS-REFERENCE TO RELATED APPLICATIONS

This application is a national stage application (under 35 U.S.C. § 371) of PCT/EP2019/072029, filed Aug. 16, 2019, which claims benefit of European Application No. 18189589.7, filed Aug. 17, 2018, both of which are incorporated herein by reference in their entirety.

The present invention relates to a process for the production of chromanol derivatives, in particular to a process for the production of compounds belonging to the vitamin E family.

BACKGROUND OF THE INVENTION

Vitamin E is the most important fat-soluble antioxidant in biological systems. The term vitamin E includes all tocol and tocotrienol derivatives having the biological activity of (2R)-2,5,7,8-tetramethyl-2-[(4R,8R)-4,8,12-trimethyltridecyl]-3,4-dihydro-2H-chromen-6-ol (1.1), which is the most relevant vitamin E for human health (see for instance W. Bonrath et al., Angew. Chem. Int. ed., 2012, 51, 12960-12990; T. Netscher, Vitamins and Hormons, 2007, Elsevier Inc. volume 76, 155).

Naturally occurring vitamin E encompasses the tocopherol compounds of formulae I.1 to 1.4 (α-, β-, γ- and δ-tocopherol) as well as the tocotrienol compounds of formulae I.5 to 1.8 (α-, β-, γ- and δ-tocotrienol).

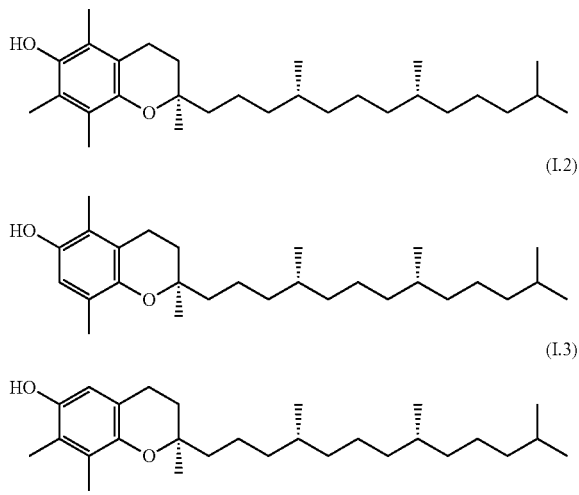

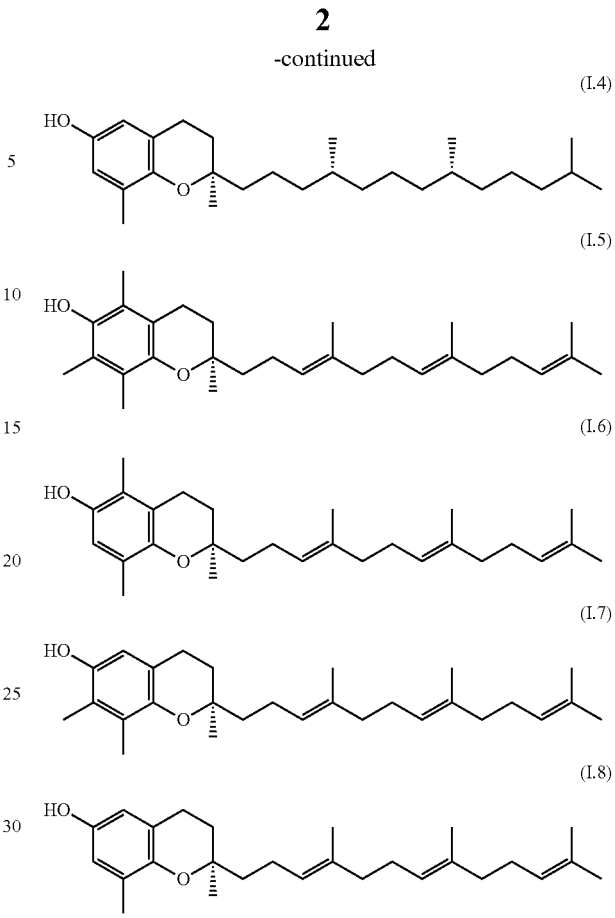

These naturally occurring compounds exist in the form of single isomers, i.e. the α-, β-, γ-, and δ-tocopherols (1.1 to 1.4) have 2R,4R,8R configuration and the corresponding α-, β-, γ-, and δ-tocotrienols (1.5 to 1.8) are present as the 2R,3E,7E isomers.

Industrially, α-tocopherol is mainly produced in the form of all racemic α-tocopherol (all-rac-I.1) and all-rac-α-tocopherol acetate (all-rac I.1a), which represent equimolar mixtures of all 8 possible stereoisomers. Typically, all-racemic α-tocopherol is synthesized via the condensation of trimethylhydroquinone (III.1) with all-racemic isophytol (all-rac-isophytol), as depicted in scheme 1. This condensation reaction involves a Friedel-Crafts alkylation of the trimethylhydroquinone (III.1) followed by a subsequent ring-closing reaction. The thus obtained all-racemic α-tocopherol (all-rac-I.1) is then transformed into the more stable acetate form (all-rac-I.1a) via esterification with acetic acid anhydride.

Scheme 1: Industrial Synthesis of all Racemic α-Tocopherol (Acetate).

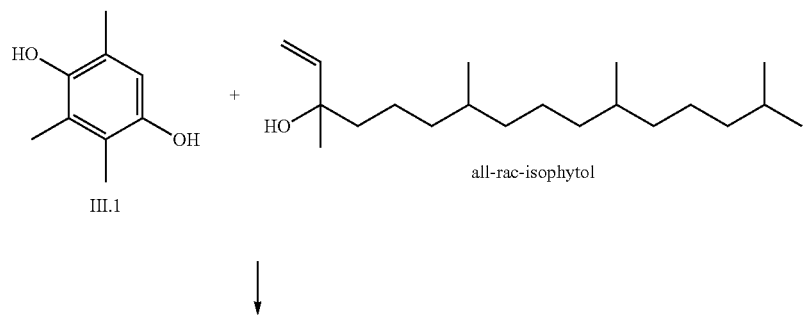

-continued

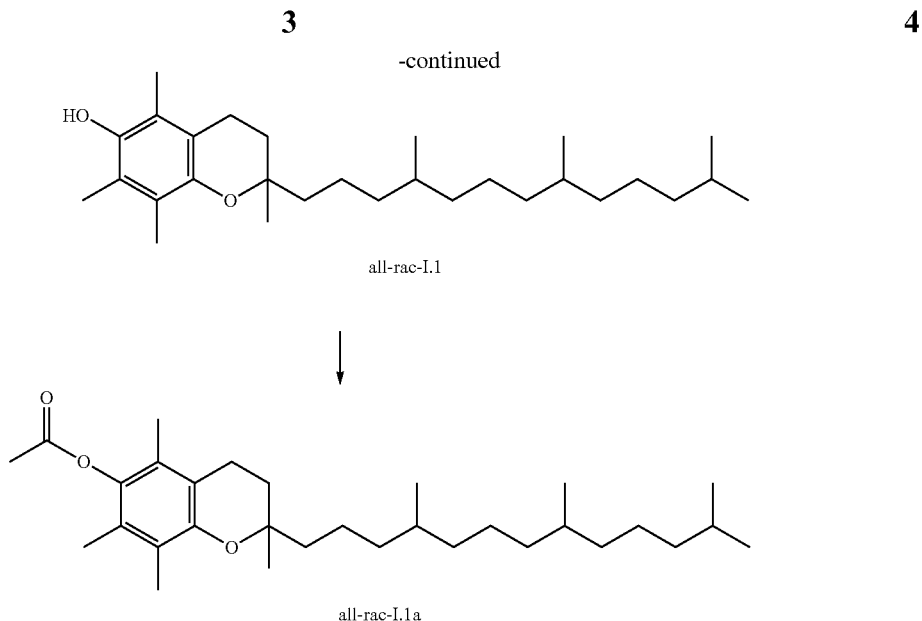

all-rac-I.1

↓ all-rac-I.1a

The other tocopherols, i.e. β-, γ- and δ-tocopherol, as well as the corresponding tocotrienols, in particular α-tocotrienol, are generally produced in analogous way.

Over the last decades, a large number of processes for the production of α-tocopherol have been developed. A key step in many of these processes is the Friedel-Crafts alkylation of the corresponding hydroquinone precursors, as depicted in scheme 1, which is performed in the presence of a Friedel-Crafts catalyst.

Generally, strong Lewis acids such as zinc chloride, aluminium chloride, tin chloride, iron chloride, titanium tetrachloride or boron trifluoroetherate and combinations of strong Lewis acids and strong Brønsted acids, such as hydrochloric acid, sulfuric acid and phosphoric acid, are used as catalysts for this Friedel-Crafts reaction.

WO 9728151 for example describes the reaction of 2,3,5-trimethylhydroquinone with isophytol to α-tocopherol in the presence of cyclic carbonate solvents by using homogeneous Brønsted acids and Lewis acids, such as orthoboric acid, oxalic acid, tartaric acid, citric acid or boron trifluoroetherate at elevated reaction temperatures in the range of from 145 to 155° C.

However, the use of these catalysts is associated with several disadvantages. First of all, they can foster the formation of by-products (e.g. the use of oxalic acid, tartaric acid or citric acid generally increases the formation of unwanted phytadienes). Furthermore, these catalysts can typically not be recovered and reused, because of their instability towards water. Furthermore, the catalysts are used in stoichiometric amounts or in a high catalytic loading. Besides, these catalysts are typically corrosive and waste containing heavy metals, such as zinc or tin, and chloride are often obtained.

In order to circumvent these disadvantages, heterogeneous catalysts have been applied as catalyst for the Friedel-Crafts alkylation.

Odinokov et al., ARKIVOC 2003, (xiii), 101-118 and Scegolev et al., UDK: 547.814.I.07 1982, VINITI 7.09.82, No. 4780-82, for example, describe the use of zeolite catalysts, such as Tseokar-10 or ASNC-ZP in the reaction of hydroquinones with tertiary isoprenoid allylic alcohols. The use of zeolites has the disadvantage, that the reactions have to be performed at high dilutions and that these zeolites are often not commercial available.

Y. Tachibana, Bull. Chem. Soc. Japan, 1977, 50 (9), 2477, describes the use of zinc chloride or tin chloride treated strongly acidic ion-exchanged resins, such as amberlyst 15, as catalyst in the reaction of trimethylhydroquinone with isophytol. However, these catalysts typically suffer from a low catalytic activity and wastes containing heavy metals and chloride are produced.

EP 677520 A1 and Matsui et al., Bull. Chem. Soc. Japan, 1996, 69, 137, describe the use of ion-exchanged bentonite, montmorillonite or saponite through treatment with scandium chloride or other metal salts, such as yttrium, lanthanum, etc., as catalyst for the reaction of trimethylhydroquinone with isophytol has the disadvantage that large amounts of catalyst are required.

DE 2404621 describes a process for the preparation of α-tocopherol by reacting trimethylhydroquinone with phytol, isophytol or a derivative thereof using a solid acid catalyst having a specific acid strength. Among others, naturally occurring minerals, which exhibit acidity, such as acid clay, bentonite, kaolin or mordenite, are mentioned as suitable catalysts. In a specific example, bentonite is used as the catalyst yielding the desired α-tocopherol in 51.8% yield. Also here, large amounts of the catalyst are required and the obtained yields are moderate.

2,3,5-Trimethylhydroquinone (111.1), which is commonly used as aromatic building block in the industrial synthesis of all racemic α-tocopherol, is typically obtained by reduction of 2,3,5-Trimethylquinone (11.1), as depicted in scheme 2.

Scheme 2:

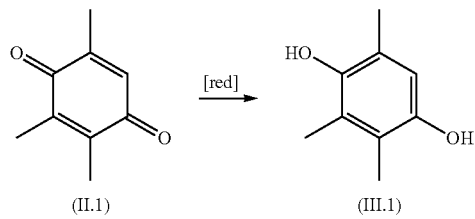

Many methods for the reduction of these quinones to the corresponding hydroquinones have been developed.

EP0264823B2 for example describes a process for the production of 2,3,5-trimethyl-hydroquinone by catalytic hydrogenation of 2,3,5-trimethylquionone in the presence of an hydrogenation catalyst selected from platinum group metals deposited on an alkali metal-containing silica alumina as a support. As suitable solvent for these catalytic hydrogenation reactions, aliphatic alcohols, aromatic alcohols, ketones, organic acids, organic acid esters, ethers, cyclic ethers, lactones and mixtures thereof, are proposed.

The main focus of the above developments is the identification of suitable reaction conditions that allow to avoid environmentally harmful reagents and catalysts and to simplify the reaction procedure, in particular to simplify the isolation of the products.

Thus, new methods and new reagents which offer alternatives to those already known are constantly being sought.

SUMMARY OF THE INVENTION

It is, thus, an object of the present invention to provide a process for the production of vitamin E derivatives starting from the corresponding benzoquinone precursors, which is efficient and which provides the desired products in high yield and selectivity, without the need to apply expensive, corrosive and/or environmentally harmful catalysts and solvents. The process should be simple and laborious purification procedures should be avoided. Besides, the process should be applicable in large-scale production and the applied catalyst should be recyclable.

It was now surprisingly found that these and further objects are achieved by a process, which comprises the catalytic hydrogenation of the benzoquinone precursors to the corresponding hydroquinones in the presence of a carbonate solvent followed by Friedel-Crafts alkylation of the thus obtained hydroquinones.

Accordingly, the present invention relates to a process for preparing a compound of the general formula I

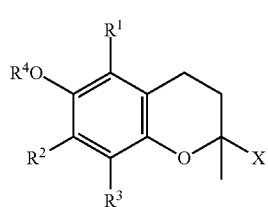

wherein
$R^1$, $R^2$ and $R^3$ independently of each other are selected from hydrogen and methyl,
$R^4$ is selected from hydrogen and $C_1$-$C_6$-alkanoyl, and
X is selected from $C_1$-$C_{20}$-alkyl and $C_2$-$C_{20}$-alkenyl, comprising the following steps:
a) providing a quinone compound of the general formula II,

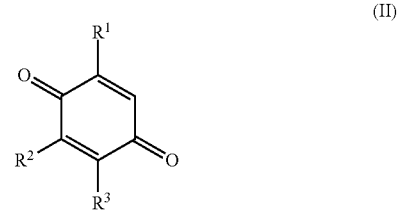

wherein $R^1$, $R^2$ and $R^3$ are as defined above,
b) catalytic hydrogenation of the quinone compound of formula II provided in step a) in the presence of hydrogen, a hydrogenation catalyst and in the presence of a carbonate solvent to obtain a hydroquinone compound of the general formula III,

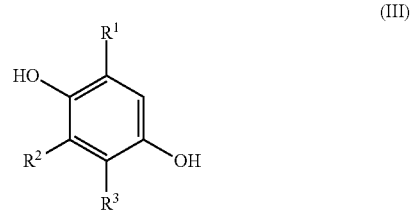

wherein $R^1$, $R^2$ and $R^3$ are as defined above,
c) reacting the hydroquinone compound III provided in step b) with an unsaturated compound of the general formula IV.a or IV.b

wherein
X is as defined above,
Y is selected from OH, halogen, —O—$R^{11}$, —S—$R^{12}$ and —$SO_2$—$R^{12}$,
$R^{11}$ is selected from $C_1$-$C_4$-alkyl, $C_1$-$C_4$-alkanoyl and trifluoroacetyl, and
$R^{12}$ is selected from $C_1$-$C_6$-alkyl, trifluoromethyl and phenyl, where phenyl is unsubstituted or substituted with 1, 2, 3, 4 or 5 radicals selected from halogen and methyl,
in the presence of a condensation catalyst, and
d) in case $R^4$ is selected from $C_1$-$C_6$-alkanoyl, reacting the condensation product obtained in step c) with a $C_2$-$C_7$-carboxylic acid or with a $C_2$-$C_7$-carboxylic acid anhydride in the presence of an esterification catalyst, or reacting the condensation product obtained in step c) with an activated $C_2$-$C_7$-carboxylic acid in the presence of a base.

DETAILED DESCRIPTION OF THE INVENTION

In the context of the present invention, the term "alkyl" as used herein refers to a linear or branched saturated hydrocarbon radical having 1 to 3 ("$C_1$-$C_3$-alkyl"), 1 to 4 ("$C_1$-$C_4$-alkyl"), 1 to 6 ("$C_1$-$C_6$-alkyl") or 1 to 20 ("$C_1$-$C_{20}$-alkyl") carbon atoms. $C_1$-$C_3$-Alkyl is methyl, ethyl, propyl and isopropyl. $C_1$-$C_4$-Alkyl is additionally n-butyl, 1-methylpropyl (sec-butyl), 2-methylpropyl (isobutyl) or 1,1-dimethylethyl (tert-butyl). $C_1$-$C_6$-Alkyl is additionally also, for example, n-pentyl, 1-methylbutyl, 2-methylbutyl, 3-methylbutyl, 1,2-dimethylpropyl, n-hexyl, 1-methylpentyl, 2-methylpentyl, 3-methylpentyl, 4-methylpentyl or 1,3-dimethylbutyl. $C_1$-$C_{20}$-Alkyl is additionally also, for example, n-heptyl, 1-methylhexyl, 2-methylhexyl, 3-methylhexyl, 4-methylhexyl, 5-methylhexyl, 2,4-dimethylpentyl, n-octyl, isooctyl, 2-ethylhexyl, n-nonyl, isononyl, n-decyl, iso-decyl, 2-propylheptyl, n-undecyl, isoundecyl, 2,4-dimethylnonyl, n-dodecyl, isododecyl, n-tridecyl, isotridecyl, tetradecyl, isotetradecyl, hexadecyl, isohexadecyl, 4,8,12-trimethyltridecyl, octadecyl, isooctadecyl and the like.

In the context of the present invention, the term "$C_1$-$C_4$-alkanoyl" denotes a $C_1$-$C_4$-alkyl group, as defined above, attached via a carbonyl [(C=O)] group to the remainder of the molecule. The term "$C_1$-$C_6$-alkanoyl" denotes a $C_1$-$C_6$-alkyl group, as defined above, attached via a carbonyl [(C=O)] group to the remainder of the molecule. $C_1$-$C_4$-alkanoyl is methylcarbonyl, ethylcarbonyl, n-propylcarbonyl, isopropylcarbonyl, n-butylcarbonyl, 1-methylpropylcarbonyl, 2-methylpropylcarbonyl or 1,1-dimethylethylcarbonyl. $C_1$-$C_6$-alkanoyl is additionally, for example, n-pentylcarbonyl, 1-methylbutylcarbonyl, 2-methylbutylcarbonyl, 3-methylbutylcarbonyl, 1,2-dimethylpropylcarbonyl, n-hexyl-carbonyl, 1-methylpentylcarbonyl, 2-methylpentylcarbonyl, 3-methylpentylcarbonyl, 4-methylpentylcarbonyl or 1,3-dimethylbutylcarbonyl.

The term "halogen" denotes in each case fluorine, bromine, chlorine or iodine, in particular fluorine, chlorine or bromine. Halogen as a substituent on phenyl is preferably Cl or Br.

The compounds obtainable by the process of the present invention are compound of the general formula I

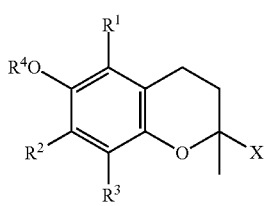

(I)

wherein
$R^1$, $R^2$ and $R^3$ independently of each other are selected from hydrogen and methyl,
$R^4$ is selected from hydrogen, $C_1$-$C_6$-alkanoyl, and
X is selected from $C_1$-$C_{20}$-alkyl and $C_2$-$C_{20}$-alkenyl.

Due to their structure, the compounds (I) can be present in the form of pure enantiomers or diastereoisomers as well as in the form of enantiomer or diastereoisomer mixtures.

The term "stereoisomers" encompasses optical isomers, such as enantiomers or diastereoisomers, the latter existing due to more than one stereogenic centre in the molecule. The compounds of the formula (I), where X is not methyl, have at least one stereogenic centre, namely the carbon atom in the 2-position of the chromane ring. Furthermore, in compounds (I) the radical X may also have at least one stereogenic centre, for example if X is selected from 4,8-dimethylnonyl or 4,8,12-trimethyltridecyl. The invention relates to both, the pure enantiomers or diastereoisomers of compounds (I) as well as to mixtures thereof.

Furthermore, in case the radical X is selected $C_2$-$C_{20}$-alkenyl, compounds (I) may also have at least one double bond, which can have E- or Z-configuration, for example if X represents the isoprenyl moieties 4,8-dimethyl-3,7-nonadienyl or 4,8,12-trimethyl-3,7,11-tridecatrienyl. Thus, the invention also relates to compounds (1), wherein the double bond(s), if present, has/have pure E- or Z-configuration and/or is/are present as E/Z-mixture(s).

Preferably, in compounds (I) and (III) of the process of the present invention, the radicals $R^1$, $R^2$ and $R^3$ have the following meanings:
$R^1$ is methyl,
$R^2$ is methyl, and
$R^3$ is methyl,
or
$R^1$ is methyl,
$R^2$ is hydrogen, and
$R^3$ is methyl,
or
$R^1$ is hydrogen,
$R^2$ is methyl and
$R^3$ is methyl,
or
$R^1$ is hydrogen,
$R^2$ is hydrogen, and
$R^3$ is methyl.

In particular, in compounds (I) and (III), the radicals $R^1$, $R^2$ and $R^3$ are methyl.

Preferably, in compounds (I) of the process of the present invention, the radical $R^4$ is selected from hydrogen and $C_1$-$C_4$-alkanoyl, more preferably from hydrogen and $C_1$-$C_2$-alkanoyl, in particular from hydrogen and ethanoyl.

Preferably, in compounds (I), (IV.a) and (IV.b) of the process of the present invention, the moiety X is selected from methyl or has one of the following meanings X-1 to X-6

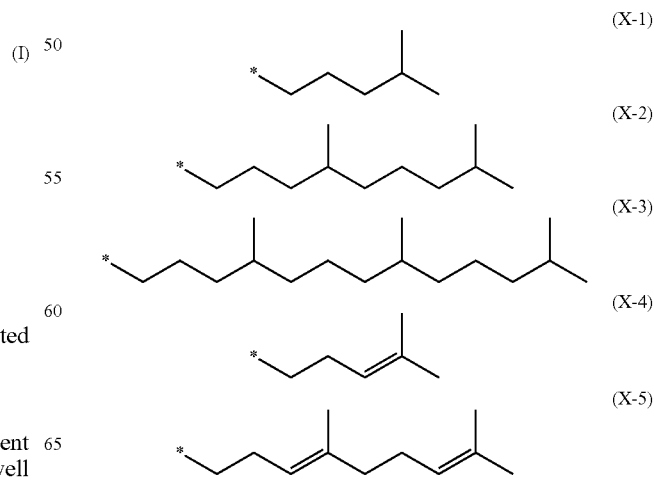

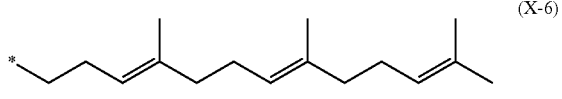
(X-6)

wherein * indicates the attachment point to the chromane ring.

In particular, in compounds (I), (IV.a) and (IV.b) of this first embodiment, the moiety X is selected from (X-3) or (X-6)

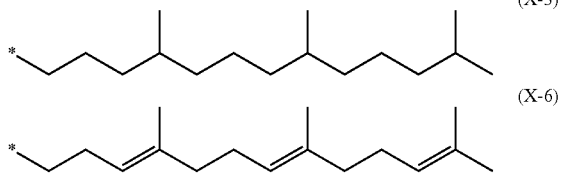
(X-3)

(X-6)

wherein * indicates the attachment point to the rest of the molecule.

In a preferred embodiment, in compounds (I)
$R^1$ is methyl,
$R^2$ is methyl, and
$R^3$ is methyl,
or
$R^1$ is methyl,
$R^2$ is hydrogen, and
$R^3$ is methyl,
or
$R^1$ is hydrogen,
$R^2$ is methyl and
$R^3$ is methyl,
or
$R^1$ is hydrogen,
$R^2$ is hydrogen, and
$R^3$ is methyl,
$R^4$ is selected from hydrogen and $C_1$-$C_4$-alkanoyl, and
X is selected from methyl or a radical of formulae X-1 to X-6.

In a more preferred embodiment, in compounds (I)
$R^1$ is methyl,
$R^2$ is methyl, and
$R^3$ is methyl,
or
$R^1$ is methyl,
$R^2$ is hydrogen, and
$R^3$ is methyl,
or
$R^1$ is hydrogen,
$R^2$ is methyl and
$R^3$ is methyl,
or
$R^1$ is hydrogen,
$R^2$ is hydrogen, and
$R^3$ is methyl,
$R^4$ is selected from hydrogen and $C_1$-$C_2$-alkanoyl, in particular from hydrogen and ethanoyl, and
X is methyl or has one of the following meanings (X-3) or (X-6)

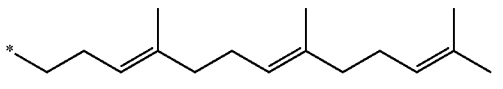
(X-3)

(X-6)

wherein * indicates the attachment point to the rest of the molecule.

In a particular embodiment, in compounds (1)
$R^1$, $R^2$ and $R^3$ are methyl,
$R^4$ is selected from hydrogen and ethanoyl, and
X has one of the following meanings (X-3) or (X-6)

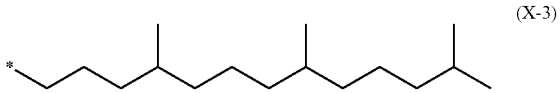
(X-3)

(X-6)

wherein * indicates the attachment point to the rest of the molecule.

Preferably, in compounds (IV.a) and (IV.b), the radical Y is selected from OH, Cl, Br, I, —O—$R^{11}$, —S—$R^{12}$ and —$SO_2$—$R^{12}$, wherein
$R^{11}$ is selected from $C_1$-$C_4$-alkanoyl and trifluoroacetyl, and
$R^{12}$ is selected from $C_1$-$C_3$-alkyl, trifluoromethyl, phenyl, 4-methylphenyl and pentafluorophenyl.

More preferably, in compounds (IV.a) and (IV.b), the radical Y is selected from OH, Br, —O—$R^{11}$, —S—$R^{12}$ and —$SO_2$—$R^{12}$, wherein
$R^{11}$ is selected from acetyl and trifluoroacetyl, and
$R^{12}$ is selected from methyl, trifluoromethyl and 4-methylphenyl.

In particular, in compounds (IV.a) and (IV.b), the radical Y is selected from OH, —O—$R^{11}$ and —$SO_2$—$R^{12}$, wherein
$R^{11}$ is selected from acetyl, and
$R^{12}$ is selected from methyl, trifluoromethyl and 4-methylphenyl.

Step a):

Step a) of the present invention comprises the provision of a quinone compound of the general formula (II).

These quinone compounds are either commercially available or can be prepared from readily available precursors by processes described in the art.

For example, 2,3,5-trimethylquinone can be prepared by catalytic methylation of m-cresol to 2,3,6-trimethylphenol (step i), followed by oxidation of the thus obtained 2,3,6-trimethylphenol using an oxidation agent (step ii)), as depicted in scheme 3.

Scheme 3:

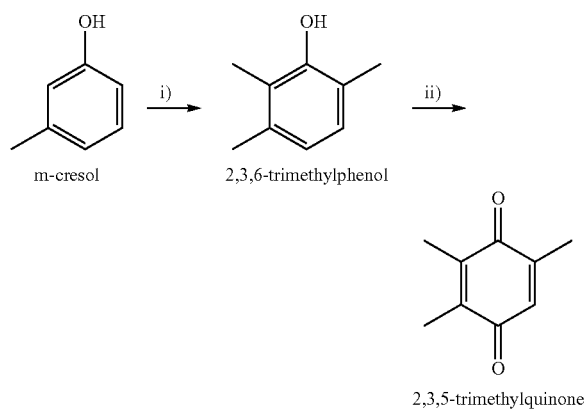

m-cresol  2,3,6-trimethylphenol 2,3,5-trimethylquinone

The catalytic methylation in step i) is typically carried out with methanol or dimethylether as the alkylating agent in the presence of a metal oxide catalyst, such as for example aluminium oxide, silicium oxide, magnesium oxide, calcium oxide, barium oxide, iron oxide, chromium oxide, zinc oxide, manganese oxide, zirconium oxide, thorium oxide, and the like, as well as mixed metal oxide catalysts.

The individual reaction conditions for the catalytic methylation of phenols, such as m-cresol, are well known to the skilled person.

The oxidation in step ii) can be conducted according to standard procedures that are well known to the skilled person. Typically, the oxidation is carried out in the presence of an oxidizing agent, optionally with the help of a metal salt or noble metal catalyst. In principle, all oxidizing agents known to the skilled person to be capable to oxidize phenols to quinones can be used in the oxidation in step ii).

Suitable oxidizing agents are for example:

hydrogen-peroxide, oxygen or an oxygen containing gas in the presence of catalytic amounts of metal salt, such as Mg(II)-, Ca(II)-, Ba(II)-, Cu(II)-, Fe(II)-, Cr(II)-, Mn(II)-, Co(II)-, Ni(II)-, Zn(II)-, sulfates or chlorides, as well as mixtures of these metal salts, or a noble metal catalyst, such as for example a ruthenium, rhodium, platinum or palladium catalyst;

mineral acids, such as nitric acid, sulfuric acid, chloric acid, hypochloric acid, perchloric acid, iodic acid or periodic acid; or organic peroxy acids, such as perbenzoic acid or meta-chloroperbenzoic acid.

Suitable reaction conditions for this oxidation reaction are well known to the skilled person.

Step b):

Step b) of the present invention comprises the catalytic hydrogenation of the quinone compound of formula II provided in step a) in the presence of hydrogen, a hydrogenation catalyst and in the presence of a carbonate solvent to obtain a hydroquinone compound of the general formula III,

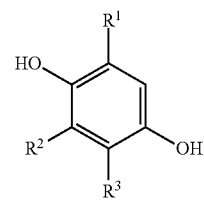

(III)

wherein $R^1$, $R^2$ and $R^3$ are as defined above.

In step b), the benzoquinone (II) is usually dissolved in the carbonate solvent and contacted with hydrogen and a hydrogenation catalyst.

Hydrogenation catalysts that can be used in the catalytic hydrogenation in step b) are those commonly used in the art to catalyse the hydrogenation of organic compounds. Some examples of these include palladium chloride on charcoal, activated nickel, nickel-nickel oxide, platinum-platinum oxide, platinum black, platinum on charcoal, copper chromite, Raney nickel, palladium, palladium black, palladium on charcoal, palladium sponge, nickel, copper impregnated alumina, activated alumina, Raney copper, chromium, vanadium, molybdenum, and the like.

Preferably the hydrogenation catalyst applied in step b) is a heterogeneous hydrogenation catalyst, more preferably a supported metal catalyst.

Suitable supports are for example carbon, carbon black, active charcoal, graphite, aluminium oxide, silicon oxide, titanium dioxide, zirconium dioxide, cerium dioxide, lanthanium(III)-oxide, zinc oxide, silicates, asbestos, silicon carbide, calcium carbonate, magnesium carbonate, magnesium sulfate, barium carbonate, barium sulfate, zeolites, diatomaceous earth, and mixtures thereof.

Even more preferably, the hydrogenation catalyst applied in step b) is a carbon supported catalyst.

In particular, the hydrogenation catalyst applied in step b) is a carbon supported noble metal catalyst, i.e. a noble metal catalyst comprising a support material based on carbon (C), for example activated carbon.

In principle, suitable carbon-based support materials are all carbon materials known to the person skilled in the art for such uses. Suitable carbon-based support materials are for example carbon, carbon black, active charcoal and graphite. The support materials may preferably be used in the form of shaped bodies, granules, strands, pellets, spall, tablets or prills. The BET surface area of the support materials (25° C.) is typically in the range from 1 to 10 000, preferably from 10 to 5000, m²/g, but is uncritical in most cases for the process of the invention.

Suitable noble metals are for example selected from Pt, Pd, Ru, Rh and Ir.

Specifically, the hydrogenation catalyst applied in step b) is selected from a carbon supported Pd catalyst, more specifically from Pd on charcoal.

The metal content of the supported metal catalyst used in step b) of the present invention is typically in the range of from 0.1% to 20% by weight, preferably in the range of from 1% to 15% by weight, based on the total weight of the carbon supported noble metal catalyst.

Typically, the amount of the hydrogenation catalyst used in step b) of the present invention is in the range of from 0.05% to 20% by weight, preferably in the range of from 0.1% to 10% by weight, more preferably in the range of from 0.2% to 5% by weight, based on the amount of quinone present in the reaction mixture.

The catalytic hydrogenation may be carried out at atmospheric pressure or at elevated pressures. Higher pressures usually result in faster hydrogenation rates. Extremely high pressures are not required because the benzoquinones are readily reduced. The catalytic hydrogenation in step b) is typically performed at a pressure in the range from 1 to 100 bar, preferably in the range from 1 to 50 bar, especially in the range from 2 to 30 bar.

The hydrogenation is carried out at a temperature high enough to promote the reduction of the benzoquinone, but not so high as to cause degradation of the reactants, reaction medium or products. The suitable reaction temperature is typically in the range of from 20 to 150° C., preferably in the range from 30 to 120° C. and especially in the range from 40 to 100° C.

According to the present invention, the catalytic hydrogenation reaction in step b) is carried out in the presence of a carbonate solvent selected from organic carbonates.

Preferably, the carbonate solvent is selected from cyclic and linear carbonates of the general formula VI.a and VI.b

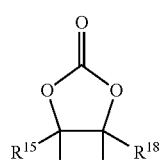

(VI.a)

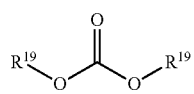

(VI.b)

wherein
$R^{15}$, $R^{16}$ and $R^{17}$ independently of each other are selected from hydrogen, methyl and ethyl, in particular from hydrogen and methyl,
$R^{18}$ is selected from hydrogen, phenyl and $C_1$-$C_{15}$-alkyl, where $C_1$-$C_{15}$-alkyl is unsubstituted or substituted with 1, 2, or 3 radicals, selected from $C_1$-$C_3$-alkoxy, polyalkyleneoxide, phenyl and phenoxy, in particular from hydrogen, phenyl, $C_1$-$C_3$-alkyl and benzyl, and
$R^{19}$ independently of each other are selected from $C_1$-$C_4$-alkyl, in particular from ethyl and n-propyl.

More preferably, the carbonate solvent is selected from cyclic and linear carbonates of the general formula VI.a and VI.b

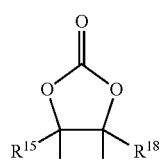

(VI.a)

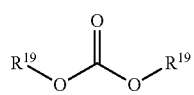

(VI.b)

wherein
$R^{15}$, $R^{16}$ and $R^{17}$ independently of each other are selected from hydrogen and methyl,
$R^{18}$ is selected from hydrogen, methyl, ethyl, phenyl and benzyl, and
$R^{19}$ independently of each other are selected from ethyl and n-propyl.

Amongst these carbonate solvents, those carbonate solvents are preferred which have a boiling point of at least 100° C., more preferably of at least 120° C., in particular of at least 140° C.

Specifically, the carbonate solvent is selected from ethylene carbonate, propylene carbonate, butylene carbonate, 2,3-propylene carbonate, isobutylene carbonate, diethyl carbonate and di-n-propyl carbonate.

These cyclic and acyclic carbonates do not give rise to any toxicological concerns, which is very important for the preparation of the compounds of the general formulae I and II. Furthermore, these solvents are well biodegradable.

The reaction in step b) may additionally be conducted in the presence of an apolar hydrocarbon solvent (HS).

Accordingly, in an alternative embodiment of the present invention, step b) is carried out in a solvent mixture consisting of at least one carbonate solvent, as defined above, and at least one apolar hydrocarbon solvent (HS).

Preferably, the apolar hydrocarbon solvent (HS), if present, is selected from the following groups:
HS.1 linear and branched alkanes having 5 to 15 carbon atoms, such as for example pentane, hexanes, heptanes, octanes, nonanes, decanes, ligroin and petrol ether;
HS.2 cycloalkanes having 5 to 10 carbon atoms, such as for example cyclohexane;
HS.3 aromatic hydrocarbons having 6 to 12 carbon atoms, such as for example benzene, toluene, xylenes, ethylbenzene and tetralin;
and mixtures thereof.

More preferably, the apolar hydrocarbon solvent (HS) is selected from the groups HS.1 and HS.2.

Specifically, the apolar hydrocarbon solvent (HS) is selected from hexane, cyclohexane, heptane, octane and nonane, more specifically from heptane and octane.

In this alternative embodiment, the content of the carbonate solvent in this solvent mixture is typically in the range of from 35 to 99% by weight, preferably in the range of from 50 to 99% by weight, in particular in the range of from 50 to 90% by weight, based on the total weight of the solvent mixture.

Accordingly, the weight ratio of the carbonate solvent to HS applied in step b) is typically in the range of from 1:3 to 100:1, preferably in the range of from 1:1 to 100:1, in particular in the range of from 1:1 to 10:1.

In this alternative embodiment, carbonate solvents are preferred, which are not or only sparingly miscible with the at least one apolar hydrocarbon solvent (HS), which means that step b) is carried out in a biphasic solvent mixture consisting of a carbonate solvent-phase and a HS-phase. In this connection, the term "sparingly miscible" means that less than 5% by weight, preferably less than 2% by weight, more preferably less than 1% by weight, in particular less than 0.5% by weight, of the polar aprotic solvent (PS) is present in the HS-phase.

In this alternative embodiment, solvent mixtures are preferred consisting of at least one carbonate solvent and at least one apolar hydrocarbon solvent of the group HS.1.

In particular, in this alternative embodiment, the solvent mixture consists of at least one carbonate solvent, selected from ethylene carbonate, propylene carbonate, butylene carbonate, 2,3-propylene carbonate, isobutylene carbonate, diethyl carbonate and di-n-propyl carbonate, and at least one apolar hydrocarbon solvent (HS), selected from heptane and octane.

In a specific embodiment of the present invention, step b) is carried out in at least one carbonate solvent (PS), as defined above.

The catalytic hydrogenation can be carried out in a variety of reactors known for this purpose, such as a serial loop reactor as described in U.S. Pat. No. 5,756,856, but also in simpler reactors, as described for example in DE 2008128. Preference is given to fixed bed reactors, in particular to trickle bed reactors.

The reaction product, i.e. the compound of formula (III), obtained in step b) is typically worked-up by filtering off the hydrogenation catalyst. The thus obtained reaction mixture can directly be used in step c) of the instant process.

If desired, the thus obtained reaction mixture can be further worked-up in a conventional way, e.g. by mixing with water, separating the phases and, where appropriate, purifying the crude products by using chromatographic methods, by distillation, or by recrystallization.

In a preferred embodiment of the present invention, the reaction mixture obtained in step b) is used directly in the reaction in step c) of the instant process, after removal of the hydrogenation catalyst.

Step c):

Step c) of the present invention comprises the reaction of the compound (III) provided in step b) with an unsaturated compound of the general formula (IV.a) or (IV.b)

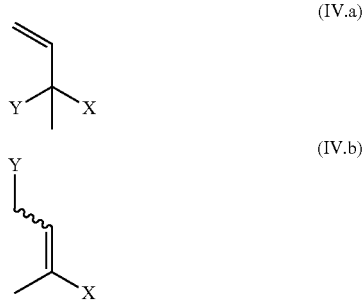

wherein

X has one of the meanings given above,

Y is selected from OH, halogen, —O—$R^{11}$, —S—$R^{12}$ and —$SO_2$—$R^{12}$, $R^{11}$ is selected from $C_1$-$C_4$-alkyl, $C_1$-$C_4$-alkanoyl and trifluoroacetyl, and $R^{12}$ is selected from $C_1$-$C_6$-alkyl, trifluoromethyl and phenyl, where phenyl is unsubstituted or substituted with 1, 2, 3, 4 or 5 radicals selected from halogen and methyl, in the presence of a condensation catalyst.

Generally, any condensation catalysts that are capable to catalyze Friedel-Crafts alkylation reactions and/or (intramolecular) hydroxyalkylations of olefins (intramolecular cyclization reaction) can be applied in step c) of the process of the present invention.

Suitable conventional condensation catalyst are for example Lewis acids, such as zinc chloride, aluminium chloride, tin chloride, iron chloride, titanium tetrachloride or boron trifluoroetherate, Brønsted acids, such as hydrochloric acid, sulfuric acid and phosphoric acid, and acidic heterogeneous catalysts, as well as combinations thereof.

In a preferred embodiment of the present invention, the condensation catalyst applied in step c) is selected from acidic heterogeneous catalysts.

Suitable acidic heterogeneous catalysts are for example selected from cation exchange resins, e.g. cation exchange resins containing sulfonic acid groups, such as amberlyst 15 or Dowex 50W; zeolites, such as H-BFA zeolites, H-Y zeolites, pentasil zeolites, Tseokar-10 or K-10 zeolites; as well as naturally occurring minerals having a certain acidity, such as acidic clay, montmorillonite, bentonites, kaolin, saponites or mordenites.

Preferable condensation catalyst applied in step c) of the present invention are selected from silicate clay minerals containing the elements H, C, O, Si, Al, Mg, Ca, Li, Na, K, Fe, Zn, S, F and all combinations thereof. Preferable silicate minerals that can be applied as condensation catalyst in step c) of the present invention are for example pyrophyllite, talc, micas (e.g. muscovite, paragonite, phlogopite, biotite, lepidolite, zinnwaldite, taeniolite, fluor-tetrasilicic mica), brittle micas (margarite, chloritoid, seyberite, clintonite), hydrous micas, illites, chlorites, vermiculites, smectites (montmorillonite, saponite, nontronite, beidellite, sauconite, hectorite, fluorhectorite), kandites, serpentines and/or palygorskites (attapulgite, sepiolite)

More preferable, the condensation catalyst applied in step c) of the present invention is selected from silicate clay minerals containing montmorillonites as described, for example in Klockmann's textbook of mineralogy, 16th edition, F. Euke Verlag 1978, pages 739-765 and in R. M. Barrer Zeolites and Clay Minerals as Sorbents and Molecular Sieves, Academic Press, and in Y. Izumi, K. Urabe, M. Onaka Zeolite, Clay, and Heteropoly Acid in Organic Reactions, VCH.

Depending on their catalytic properties in their natural occurring or manufactured form, these heterogeneous condensation catalysts can be applied in untreated form or they can be treated prior to their use, in order to modify their catalytic properties. In this regard, the expression "treated" refers to a chemical treatment. Generally, the chemical treatment of the heterogeneous condensation catalysts comprises acid treatment, alkaline treatment, metal salt treatment (cation exchange) or organic treatment. Preferably the chemical treatment of the heterogeneous condensation catalysts comprises metal salt treatment (cation exchange) or an acid treatment. Acid treatment of the heterogeneous condensation catalysts is typically performed with strong Brønsted acids and/or Lewis acids.

In an even more preferred embodiment of the present invention, the reaction in step c) is carried out in the presence of a treated bentonite catalyst.

Bentonite is formed of highly colloidal and plastic clay. Bentonite is often used as a thickener and filler for paints, as an additive for ceramics and also for health products (e.g. cosmetics, nutrition or pharmaceuticals). Bentonites are good adsorbents and are characterized by high cation exchange capacity, strong swelling capacity and low permeability.

Typically, the main component of bentonite is montmorillonite, a clay mineral of the smectite group. Montmorillonite consists of two layers of silicon tetrahedrons with a central layer of one aluminium octahedron between them. It has hydroxyl groups between the layers as well as on the surface.

In principle, all deposits containing montmorillonite, as for example listed in the monograph "The Economics of Bentonite", 8th Edition 1997, Roskill Information Services Ltd, London, can be considered as suitable source of bentonites. Depending on their origin, bentonites may contain, besides montmorillonite, different amounts of a variety of accompanying minerals, as defined above, and non-mineral components.

Such accompanying minerals and non-mineral components are in particular quartz, feldspar, kaolin, muscovite, zeolites, titanium oxides, iron oxides, illites, mica calcite and/or gypsum. Preferred raw materials are those with a high montmorillonite content and a correspondingly low content of secondary components, since the amount of pure montmorillonite in the bentonite determines its performance. The higher the contents of the montmorillonite in the bentonite, the better will be its performance as an industrial raw material. The montmorillonite content can be determined, for example, by methylene blue adsorption.

Preferred raw materials have a methylene blue value of at least 250 mg/g, preferably at least 290 mg/g, in particular at least 320 mg/g. Particularly preferred raw materials are those whose exchangeable cations consist to a high percentage of alkali metals, in particular sodium. In terms of charge equivalents, these raw materials contain at least 25%, preferably at least 40%, of monovalent exchangeable cations. These sodium bentonites raw materials are found in nature, known sources for bentonites containing sodium are e.g. in Wyoming/USA or in India, they are also known by their origin as "Western Bentonites", "Wyoming bentonites" or by their properties as "swelling Benonites". Bentonites with a high proportion of alkaline earth cations, especially calcium, are known as "Subbentonites" or "Southern Bentonites" and can be converted to sodium-containing bentonites by alkaline activation.

Finally, it is in principal also possible to produce suitable synthetic clay minerals e.g. by pillaring with organic or metal complex cations (PILCs) and use them for the current invention (M. M. Herling et al. Z. Anorg. Allg. Chem. 2014, 640, 3-4. 547-560; G. Poncelet and J. J. Fripiat Handbook of Heterogeneous Catalysis ($2^{nd}$ Edition) 2008, 1, 219-247).

Clay minerals of natural origin may, in addition to the mineral impurities, also contain non-mineral impurities, especially carbon compounds. Preferred raw materials are bentonites with a total carbon content of less than 3 wt. %, preferably less than 1 wt. %, particularly preferably less than 0.5 wt. %.

It is well known that the macroscopic properties and applicability of bentonites are closely related to the amount and quality of the montmorillonite contained therein, to their pH-value (residual acidity), particle size and their porous microstructure (e.g. surface area, porosity).

Bentonites can be divided into natural bentonites, i.e untreated bentonites, and treated bentonites (see for example J. Nones et al., Applied Clay Science, 2015, 105-106, 225-230). In a preferred embodiment of the present invention, the reaction in step c) is carried out in the presence of a treated bentonite catalyst.

The term "treated bentonite", as used herein, refers to bentonites, where the structure, texture and other properties of the bentonite are modified by chemical treatment and/or heat treatment. Thus, the term "treated bentonite", as used herein, refers to chemically treated and/or heat treatment bentonite. Generally, the chemical treatment of bentonites comprises acid treatment, alkaline treatment or organic treatment. The bentonites obtained by an acid treatment or alkaline treatment are also called "activated bentonites" (acid activated bentonites or alkaline activated bentonites).

The term "acid treated bentonite" or "acid activated bentonites", as used herein, refers to bentonites, which are treated with a Brønsted acid, e.g. a mineral acid, such as HCl or $H_2SO_4$, $H_3PO_3$, $HNO_3$, boric acid, silicic acid, carboxylic acids, such as formic acid or acetic acid, or other organic acids, such as trifluoroacetic acid, methane sulfonic acid, toluene sulfonic acid or trifluoromethane sulfonic acid. Preference is given to HCl and/or $H_2SO_4$ or mixtures of HCl and/or $H_2SO_4$ with other inorganic or organic acids. Typically, acid-activated bentonites are used on a large scale as bleaching earths for the discoloration of oils.

The treatment with mineral acid is also known to impart surface acidity of the clay, which improves its catalytic properties (P. Komandel, Applied Clay Science, 2016, 131, 84-99; D. A. D'Amico et al. Applied Clay Science, 2014, 99, 254-260). Without being bound to theory, it is believed that during acid treatment or acid activation, respectively, the edges of the silicate sheets of the clay minerals in the bentonite are opened and the $Al^{3+}$ and $Mg^{2+}$ cations of the octahedral sheet become soluble. The chemistry of this activation process, where an acidic hydrogen ion, e.g. an acidic hydrogen ion from sulfuric acid, opens the sheet structure of the clay minerals in the bentonite and forms acid sites, is for example illustrated in J. Amorim et al. Hydrocarbon Engineering 2016, 21, 11, 83-8. The final acid treated bentonites contain amorphous, porous, protonated and hydrated silica with a three-dimensional cross-linked structure (P. Komandel Applied Clay Science, 2016, 131, 84-99).

Processes for the production of acid-activated clay minerals, in particular layered silicates, such as bentonites, are well known in the art; an overview is for example provided by EP0398636 (B1) and a detailed process for the acid activation of clay minerals, such as bentonites, can for example be found in DE10245198 (A1).

Alkaline treatment of bentonites relates to a treatment of the bentonites with mineral bases, such as NaOH, KOH or sodium carbonate, or organic bases, such as ammonia, trimethylamine or tetraalkylammonium hydroxides. Alkaline activation is typically performed by treatment with sodium carbonate.

The organic treatment of bentonites relates to a treatment of the bentonites with organic compounds, such as quaternary ammonium cations (e.g. alkylammonium and α-ω-dialkylammonium).

Further organic and inorganic compounds that are exchanged into the above described minerals include: hydrazine, urea, formamide, acetamide, the Li, Na, K, Rb, Cs and $NH_4$ salts of lower fatty acids (acetates, propionates, cyanoacetates), oxalate, glycollate, alaninate, lysinate, lactate, glycerine, acetylacetone, α-methoxyacetyl-acetone, acetoaceticethylester, nonanetrione-2:5:8, hexanedione-2:5, β:β'-oxydi-propionitrile, β-ethoxypropionitril, tetracyanoethylene, 7,7,8,8-tetracyanoquinomethane, bis-(2-ethoxyethyl)-ether, bis-(2-methoxyethyl)-ether, ethyleneglycoldiglycid ether, triethyleneglycol, diethyleneglycol, triethyleneglycoldiacetate, diethylenegylcoldiacetate, hexandiol-1:6, pentanediol-1:5,2:4-hexadiynediol-1:6.

Further organic bases that are exchanged into the above described minerals are amines like n-propylamine, n-butylamine, n-hexylamine, n-octylamine, benzidine, N,N,N',N'-tetramethylbenzidine, diethylamine, triethylamine, triphenylamine, p-phenylenediamine, N,N'-dimethyl-p-phenylenediamine, N,N,N',N'-tetramethyl-p-phenylenediamine, trans-4,4'-diaminostilbene dihydrochloride, benzylamine, aniline, o-toluidine.

Further long-chain alkylammonium salts that are exchanged into the above described minerals are 1-n-alkyl pyridinium bromides and cetyltrimethyl ammonium bromide.

Furthermore, glycine and its peptides, a variety of other amino-acids and ligands that are exchanged into the above described minerals are described in R. M. Barrer Zeolites and Clay Minerals as Sorbents and Molecular Sieves, Academic Press and references cited therein.

Generally, the "treated bentonite catalyst" is selected from acid treated bentonites, i.e. bentonites treated with Brønsted acids. Preferably, the "treated bentonite catalyst" is selected from bentonites treated with mineral acids as well as from bentonites treated with strong organic acids. In particular, the "treated bentonite catalyst" is selected from bentonites treated with mineral acids.

These bentonite catalysts do not cause corrosion problems for the reaction apparatus or a contamination of waste water with metal ions or inorganic acids and are sufficiently acidic to carry out the reaction in step c) in reasonable to high reaction rates.

Acid treated bentonites are either commercially available or they can be prepared using processes that are well described in the art, as illustrated above.

Commercially available acid treated bentonites (e.g also known as acid leached bentonites having the CAS-No. 70131-50-9) that can be applied as catalysts in the reaction in step c) are for example:

- montmorillonite K 10, montmorillonite K 30, montmorillonite (Aluminum pillared clay) (CAS 139264-88-3), montmorillonite-KSF (CAS 1318-93-0), obtainable e.g. from Sigma-Aldrich;
- TONSIL™ catalysts from the company Clariant Produkte (Deutschland) GmbH.

Typically, the treated bentonite catalyst has a BET surface area in the range of from 50 to 800 $m^2/g$, preferably in the range of from 100 to 600 $m^2/g$, more preferably in the range of from 120 to 500 $m^2/g$, in particular in the range of from 150 to 400 $m^2/g$. The expression "BET surface area", as used herein, refers to the well-known Brunauer-Emmett-Teller method of determining surface area. The BET surface area values given in the present application are determined via nitrogen adsorption by the BET method by largely following DIN 66131 (1973), as described in detail below.

Typically, the treated bentonite catalyst has a residual acidity, measured as mg KOH/g bentonite by titration with potentiometric indication, in the range of from 3 to 70, preferably in the range of from 5 to 50, more preferably in the range of from 10 to 45, in particular in the range of from 15 to 40. The residual acidity (mg KOH/g bentonite) is determined by following standard procedures, as described in the experimental section below.

In brief, the determination of the residual acidity of the treated bentonite catalyst is conducted in such a way that first an aqueous suspension with a certain amount of bentonite catalyst is prepared. An aqueous NaOH solution with a defined concentration is then titrated to this aqueous bentonite suspension until the pH value of the bentonite suspension switches to the alkaline range (pH >7.0), which represents to the end-point of the titration. The pH value is determined potentiometrically by means of a previously calibrated KCl-pH electrode (potentiometric indication). Then, the amount of NaOH that was necessary to reach the end-point of the titration (in milligrams) per gram of the bentonite catalyst applied in the aqueous suspension is calculated. This calculated value corresponds to the residual acidity in mg KOH/g bentonite.

Typically, the amount of free moisture in the treated bentonite catalyst is at most 30% by weight, preferably at most 25% by weight, more preferably at most 20% by weight.

The amount of free moisture in the treated bentonite is determined by weighing the individual bentonite against an anhydrous sample of the same bentonite. The anhydrous sample is obtained by drying in a vacuum oven at a temperature in the range of 100 to 200° C., optionally under reduced pressure of below 200 mbar, preferably at a temperature in the range of 100 to 150° C. and under reduced pressure of below 10 mbar, in particular of below 1 mbar, until constant weight.

In this more preferred embodiment, the amount of treated bentonite catalyst applied in step c) of the process according to the present invention is in the range of from 1 to 750 g per mol of the unsaturated alkanol of the general formula IV.a or IV.b applied in step c). Preferably, the amount of treated bentonite catalyst applied in step c) is in the range of from 5 to 500 g per mol of the compound IV.a or IV.b., more preferably in the range of from 10 to 250 g per mol of the compound IV.a or IV.b., even more preferably in the range of from 15 to 200 g per mol of the compound IV.a or IV.b, in particular in the range of from 20 to 150 g per mol of the compound IV.a or IV.b applied in step c).

Typically, the weight ratio of the treated bentonite catalyst to the compound (III) applied in step c) is in the range of from 0.01:1 to 2.5:1, preferably in the range of from 0.03:1 to 1.3:1, more preferably in the range of from 0.04:1 to 1:1 in particular in the range of from 0.05:1 to 0.7:1.

The porous structure of bentonite can further be altered by means of hydration and dehydration processes, as it is the case with heat activation, for example (L. A. Shah et al. Applied Clay Science, 2018, 162, 155-164).

In a particular preferred embodiment of the present invention, the treated bentonite catalyst is subjected to a drying step before its use in step c).

The drying step is usually carried out at a temperature in the range of from 50 to 200° C., preferably in the range of from 70 to 170° C., in particular in the range of from 80 to 150° C., especially in the range of from 100 to 120° C.

The drying step can generally be performed at ambient pressure or at reduced pressure. It is preferable that the drying step is carried out at reduced pressure.

Specifically, drying step is carried out at a pressure in the range of from 0.1 to 500 mbar, more specifically in the range of from 1 to 200 mbar.

The drying time of the treated bentonite catalyst depends on the temperature and pressure applied in the drying step and can, thus, vary over a broad range. Typically, the drying time of the treated bentonite catalyst is in the range of from several minutes to several days but is preferably in the range of from 30 minutes to 2 days.

The reaction in step c) is usually carried out at a temperature in the range of from 50 to 200° C., preferably in the range of from 70 to 170° C., in particular in the range from 80 to 150° C.

The reaction in step c) can generally be carried out at ambient pressure or at elevated or at reduced pressure.

The reaction in step c) can take place in the absence of or in the presence of an inert gas. The expression "inert gas", as used herein, generally means a gas, which under the prevailing reaction conditions does not enter into any reactions with the starting materials, reagents, or solvents participating in the reaction, or with the resultant products. It is preferable that the reaction in step c) takes place in the presence of an inert gas, preferably in the presence of argon or nitrogen, in particular in the presence of nitrogen.

The reaction in step c) is typically carried out in the presence of an organic solvent.

Preferably, the solvent applied in step c) of the present invention is selected from at least one polar aprotic solvent (PS) as well as from solvent mixtures, consisting of at least one polar aprotic solvent (PS) and at least one apolar hydrocarbon solvent (HS), as defined above.

Suitable polar aprotic solvents (PS) are for example selected from the following groups:

PS.1 organic carbonates, i.e. linear and cyclic carbonates, such as for example ethylene carbonate (243° C.), propylene carbonate, butylene carbonate, 2,3-propylene carbonate, isobutylene carbonate, dimethyl carbonate (90° C.), diethyl carbonate (128° C.) and di-n-propyl carbonate;

PS.2 ketones, such as for example diethylketone (102° C.) or methylisobutylketone (116° C.);

PS.3 lactones, such as for example γ-butyrolactone (204-206° C.);

PS.4 lactams, such as for example N-methyl-2-pyrrolidone (NMP, 203° C.);

PS.5 nitrils, such as for example acetonitril (82° C.) and valeronitril (117° C.);

PS.6 nitro compounds, such as for example nitromethan (101° C.);

PS.7 tertiary carboxamides, such as for example dimethylformamide (153° C.);

PS.8 urea derivatives, such as for example tetramethylurea (177° C.) and dimethylpropyleneurea (DMPU, 247° C.);

PS.9 sulfoxides, such as for example dimethylsulfoxide (DMSO, 189° C.);

PS.10 sulfones, such as for example sulfolane (285° C.)

PS.11 alicyclic ethers, such as for example 1,4-dioxane (101° C.);

PS.12 glycol ethers, such as for example alkylene glycol dialkyl ethers, dialkylene glycol dialkyl ethers and polyalkylene glycol dialkyl ethers;

and mixtures thereof.

Amongst these groups, those polar aprotic solvents (PS) are preferred which have a boiling point of at least 100° C., more preferably of at least 120° C., in particular of at least 140° C.

More preferably, the polar aprotic solvent (PS) is selected from the groups PS.1, PS.3, PS.4, PS.7, PS.8, PS.9, PS.10 and PS.12, even more preferably from PS.1, PS.7, PS.8 and PS.12, even more preferably from PS.1 and PS.12, in particular from PS.1.

Specifically, the polar aprotic solvent (PS) is selected from cyclic and linear carbonates of the general formula VI.a and VI.b, as defined above.

Preferably, the apolar hydrocarbon solvent (HS) is selected from the groups HS.1 and HS.2.

More preferably, the apolar hydrocarbon solvent (HS) is selected from hexane, cyclohexane, heptane, octane and nonane, more specifically from heptane and octane.

In a preferred embodiment of the present invention, step c) is carried out in a solvent mixture consisting of at least one polar aprotic solvent (PS), as defined above, and at least one apolar hydrocarbon solvent (HS), as defined above.

In this preferred embodiment, the content of the PS in the solvent mixture is typically in the range of from 35 to 99% by weight, preferably in the range of from 50 to 99% by weight, in particular in the range of from 50 to 90% by weight, based on the total weight of the solvent mixture.

Accordingly, the weight ratio of the PS to HS applied in step c) is typically in the range of from 1:3 to 100:1, preferably in the range of from 1:1 to 100:1, in particular in the range of from 1:1 to 10:1.

In this preferred embodiment, polar aprotic solvents (PS) are preferred, which are not or only sparingly miscible with the at least one apolar hydrocarbon solvent (HS), which means that step c) is carried out in a biphasic solvent mixture consisting of a PS-phase and a HS-phase. In this connection, the term "sparingly miscible" means that less than 5% by weight, preferably less than 2% by weight, more preferably less than 1% by weight, in particular less than 0.5% by weight, of the polar aprotic solvent (PS) is present in the HS-phase.

In this preferred embodiment, solvent mixtures are preferred consisting of at least one polar aprotic solvent of the group PS.1 and at least one apolar hydrocarbon solvent of the group HS.1.

In particular, in this preferred embodiment, the solvent mixture consists of at least one polar aprotic solvent (PS), selected from ethylene carbonate, propylene carbonate, butylene carbonate, 2,3-propylene carbonate, isobutylene carbonate, diethyl carbonate and di-n-propyl carbonate, and at least one apolar hydrocarbon solvent (HS), selected from heptane and octane.

In a specific embodiment of the present invention, step b) is carried out in at least one polar aprotic solvent (PS), as defined above.

The compounds of the general formulae (III) applied in step c) are highly soluble in the polar aprotic solvent (PS-phase), whereas the apolar reaction product obtained in step c), i.e. the alkylation or condensation product, which typically separates from the polar aprotic solvent as soon as the reaction mixture is cooled, is highly soluble in the apolar hydrocarbon solvent (HS-phase). Thus, the use of the above mentioned solvent mixtures has the advantage that the reaction mixture obtained in step c) can easily be separated by phase separation into a PS-phase, comprising the majority or essentially all of the unreacted compound (III) as well as the condensation catalyst, and a HS-phase, comprising the majority or essentially all of the apolar reaction product obtained in step c). If necessary, the separation of the apolar reaction product obtained in step c) from the PS-phase can be completed by extraction with the apolar hydrocarbon solvent (HS). The separated PS-phase can then be returned into the reaction in step c) or reused later in another reaction in step c). The separated HS-phase can be directly subjected to the next process step or to a purification step. Furthermore, the water formed during the reaction in step c) can easily be distilled off from the PS-phase allowing an easy recycling of the polar aprotic solvent (PS). In addition, the use of an apolar hydrocarbon solvent (HS) allows an efficient distillative removal of the water formed during the reaction in step c) through the formation of an azeotropic mixture.

In a particularly preferred embodiment of the present invention, step c) is carried out in the same carbonate solvent or the same carbonate solvent/apolar hydrocarbon solvent mixture used in step b).

The concentration of the compound (III) in the polar organic solvent (PS) is typically in the range of from 2 to 50% by weight, preferably in the range of from 3 to 45% by weight, in particular in the range of from 5 to 40% by weight.

The molar ratio of the compound (III) to the compound IV.a or IV.b applied in step c) is typically in the range of from 1:1 to 10:1, preferably in the range of from 1.05:1 to 5:1, more preferably in the range of from 1.05:1 to 3:1, in particular in the range of from 1.1:1 to 2:1.

The compounds of the general formula IV.a and IV.b are either commercially available or can be prepared from readily available precursors by processes described in the art, or can be obtained from natural sources.

For example the compounds IV.a and IV.b, wherein Y is hydroxyl are readily commercially available or can be obtained from natural sources. Compounds IV.a and IV.b, wherein Y represents a leaving group different from hydroxyl, as defined above, can be produced from the corresponding alcohol precursors via conventional nucleophilic substitution reactions. These nucleophilic reactions can be performed under conventional reaction conditions that are well known to the skilled person.

Typically, the reaction in step c) of the process of the present invention first proceeds under formation of the Friedel-Crafts alkylation product. In case the hydroxyl groups adjacent to the alkylation position are unprotected, the Friedel-Crafts alkylation reaction is typically accompanied by a following ring-closing reaction (intramolecular hydroxyalkylation of the double bond) to form a condensed six-membered cycle containing an oxygen atom. If desired, the intermediate Friedel-Crafts alkylation product can also be isolated and the ring-closing reaction can be performed in a separate step. However, it is preferable that the Friedel-Crafts-alkylation and the ring-closing reaction are performed in a single step.

In a preferred embodiment of the present invention, the reaction in step c) is performed with distillative removal of at least one portion of the water formed during the reaction.

As already mentioned above, the distillative removal of the water formed during the reaction can be facilitated by using an apolar hydrocarbon solvent (HS), such as cyclohexane, heptane, octane or toluene, in addition to the polar aprotic solvent (PS) in step c), since apolar hydrocarbon solvents (HS) often form azeotropic mixtures with water. To this end, a vapor is removed from the reaction system and is condensed. In case the vapor consists of an azeotropic mixture of water with the organic solvent applied in step c) and/or another component of the reaction mixture of step c), or the water comprises significant amounts of product or starting material, the resultant condensate is typically subjected to phase separation to give an aqueous phase and an organic phase. For this, the condensate is typically passed into a phase separator (decanter) where mechanical settling causes it to break down into two phases which can be extracted separately. If necessary, a water immiscible organic solvent, preferably the organic solvent applied in step c), is added to the condensate before passing the condensate into a phase separator. The aqueous phase is removed and discarded and the organic phase is at least to some extent returned to the reaction system. "Return to the reaction system" means that the organic phase is passed into any desired at least one reactor of the reaction system.

Any of the suitable condensers can be used for the condensation or partial condensation of the vapor. These can be cooled by any desired coolants. Preference is given to condensers with air cooling and/or water cooling, particular preference being given here to air cooling.

The reaction in step c) can be performed either in batch wise (discontinuous mode), as described above, or continuous mode. Preference is given to performing the reaction in step c) in continuous mode.

If the reaction in step c) is conducted in the batch wise (discontinuous) mode, the reactants and the catalyst are typically placed in a suitable reaction vessel, e.g. a stirred vessel or loop reactor, at the temperatures indicated above until the desired conversion is reached. The reaction time can be 0.5 to 30 hours, preferably 1 to 20 hours, depending on the amount of catalyst added.

Preferably, the reaction in step c) is conducted in such a way that first the organic solvent and the condensation catalyst, preferably the acidic heterogeneous catalyst, in particular the treated bentonite catalyst, are placed into a suitable reaction vessel, e.g. a stirred vessel or loop reactor, and heated to reaction temperature. Optionally, the resulting suspension is kept at reaction temperature for several minutes, e.g. for 1, 2, 5, 10, 15 or 20 minutes before the suspension is cooled to below 80° C. During these pretreatment steps, an inert gas, preferably argon or nitrogen, is introduced into the apparatus to ensure that the apparatus is oxygen-free. Afterwards, compound (III) is added in one portion to the preheated solvent/catalyst suspension and the resulting mixture is heated to reaction temperature. Following this, the compound IV.a or IV.b is added to the reaction mixture, optionally dissolved in an apolar hydrocarbon solvent (HS). Typically, the compound IV.a or IV.b is added stepwise to the reaction mixture, comprising the organic solvent, the condensation catalyst and the compound (III), in several portions, e.g. in 2, 3, 4, 5, 10, 15 or 20 portions, or is metered in continuously. Preferably, the compound IV.a or IV.b is metered in continuously. The addition rate of the compound IV.a or IV.b to the reaction mixture is typically in the range of from 0.2 to 5% by volume/min, preferably in the range of from 0.3 to 3% by volume/min, in particular in the range of from 0.5 to 2% by volume/min, based on the total volume of the compound IV.a or IV.b.

Depending on whether a polar aprotic solvent (PS) alone or a mixture consisting of a polar aprotic solvent (PS) and an apolar hydrocarbon solvent (HS) is applied as the organic solvent in step c), the desired reaction product is separated from the obtained reaction mixture by phase separation and/or by extraction with an apolar hydrocarbon solvent (HS). In this way, two phases are obtained, i.e. a PS-phase, comprising mainly the condensation catalyst and eventually unreacted compound (III), and a HS-phase, comprising mainly the desired reaction product and eventually unreacted compound IV.a or IV.b. After phase separation and/or extraction, the reaction product can be purified by chromatographic methods, distillation and/or crystallization, preferably by distillation, or the reaction product can be directly subjected to the next reaction step d).

In case a homogeneous condensation catalyst is used in step c) of the instant process, the reaction mixture can also be neutralized with an aqueous alkaline solution and/or with water, to remove the homogeneous condensation catalyst from the reaction mixture by extraction.

In case an acidic heterogeneous catalyst, in particular a treated bentonite catalyst, is used in step c) of the instant process, the acidic heterogeneous catalyst, in particular the treated bentonite catalyst is preferably separated from the reaction mixture or the PS-phase after completion of the reaction and reused in a further reaction in step c).

For the separation of the acidic heterogeneous catalyst, in particular the treated bentonite catalyst, from the reaction mixture or the PS-phase, generally all processes known to the skilled person that are suitable to separate solids from liquid mixtures can be used. Preferably, the catalyst is removed from the obtained reaction mixture by filtration. After separation, the acidic heterogeneous catalyst, in particular the treated bentonite catalyst, is dried in an inert gas stream, preferably in a nitrogen stream. The drying time of the acidic heterogeneous catalyst, in particular the treated bentonite catalyst, in the inert gas stream can vary over a broad range, depending on the nature of the solvent applied in the reaction in step c). The drying time of the acidic heterogeneous catalyst in the inert gas stream is typically in the range of from a few minutes to several days, i.e. from 5 minutes to 5 days. The drying time of the acidic heterogeneous catalyst in the inert gas stream can for example be 10 minutes, 30 minutes 1 hour, 5 hours, 12 hours, 1 day, 3 days or 5 days.

In another preferred embodiment of the present invention, the PS-phase, comprising mainly the condensation catalyst and eventually unreacted compound (III), which is obtained after phase separation and/or extraction of the reaction mixture obtained in step c) with an apolar hydrocarbon solvent (HS), is directly reused in a further reaction in step c).

The continuous reaction is generally carried out in at least one reactor, e.g. 1, 2, 3, 4 or 5 reactors, preferably in one reactor, comprising the treated bentonite catalyst in the form of a fixed bed or moving bed, preferably in the form of a fixed bed, into which, for example, a mixture of the organic solvent with the compound Ill and the compound IV.a or IV.b are fed. In the preferred fixed-bed operation mode, the reactor can be operated in sump operation mode, i.e. the reaction mixture is guided from bottom to top, or in the trickle operation mode, i.e. the reaction mixture will be guided through the reactor from top to bottom. The water formed during the reaction is removed by drawing off a vapor from the top of the reactor, which is condensed and separated into an organic phase, eventually comprising the apolar hydrocarbon solvent (HS) and minor amounts of unreacted compound Ill and/or reaction product, and a water phase, as described above. The organic phase is optionally returned to the at least one reactor. A stream of the reaction mixture, comprising the polar aprotic solvent (PS), the apolar hydrocarbon solvent (HS), if present, the reaction product and eventually non-reacted compound Ill is drawn off from the bottom of the reactor. Depending on whether a polar aprotic solvent (PS) alone or a mixture consisting of a polar aprotic solvent (PS) and an apolar hydrocarbon solvent (HS) is used as the organic solvent in step c), the desired reaction product is separated from the obtained reaction mixture by phase separation and/or by extraction with an apolar hydrocarbon solvent (HS). The reaction product can then be purified or the reaction product can be directly subjected to the next reaction step.

The catalyst hourly space velocity in the reaction in step c) is preferably in the range from 0.1 to 50 kg of compound IV.a or IV.b per kg of catalyst and hour, in particular in the range of from 0.2 to 30 kg of compound IV.a or IV.b per kg of catalyst and hour.

The at least one reactor may be selected from any desired reactors which are suitable for carrying out heterogeneously catalyzed chemical reactions in liquid phase.

Suitable reactors are non-back-mixed reactors, such as tubular reactors or dwell-time containers provided with internals, but preferably back-mixed reactors such as stirred-tank reactors or loop reactors. However, it is also possible to use combinations of successive back-mixed reactors and non-back-mixed reactors.

Optionally, several reactors can also be combined in a multistage apparatus. Such reactors are, for example, loop reactors with incorporated sieve trays, cascaded containers, tubular reactors with interim feed point or stirred columns.

Step d):

In case $R^4$ in compound I is selected from $C_1$-$C_6$-alkanoyl, the condensation product obtained in step c) is reacted with a $C_2$-$C_7$-carboxylic acid or with a $C_2$-$C_7$-carboxylic acid anhydride in the presence of an esterification catalyst.

Suitable esterification catalysts that can be applied in step d) of the instant process are well known to the skilled person.

Suitable esterification catalysts are for example metal based catalysts, e.g. iron, cadmium, cobalt, lead, zinc, antimony, magnesium, titanium and tin catalysts in the form of metals, metal oxides or metal salts, such as metal alcoxylates; mineral acids, such as sulfuric acid, hydrochloric acid or phosphoric acid; or organic sulfonic acids, such as methane sulfonic acid or para-toluene sulfonic acid.

Alternatively, the condensation product obtained in step d) is reacted with an activated $C_2$-$C_7$-carboxylic acid in the presence of a base.

Suitable activated $C_2$-$C_7$-carboxylic acids that can be applied in step d) of the instant process are for example $C_2$-$C_7$-carboxylic acid halides, such as $C_2$-$C_7$-carboxylic acid chlorides, -bromides or -iodides.

Suitable bases that can be applied in in step ii) are for example organic bases, such as for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

The individual reaction conditions for these esterification reactions are well known to the skilled person.

Preferably, in step d) of the instant process, the condensation product obtained in step b) is reacted with a $C_2$-$C_7$-carboxylic acid or with a $C_2$-$C_7$-carboxylic acid anhydride in the presence of an esterification catalyst.

In a preferred embodiment of the present invention, the esterification catalyst used in step d) is selected from acidic heterogeneous catalysts, as defined above.

In a more preferred embodiment of the present invention, step d) is conducted in the presence of the same acidic heterogeneous catalyst as applied in step c).

Preferably, in this more preferred embodiment, the acidic heterogeneous catalyst used in steps c) and d) is separated from the reaction mixture after completion of the reaction in step d) and reused in a further reaction in step c). The recycling of the heterogeneous condensation catalysts is performed as describe above in step c) for the treated bentonite catalyst.

In an even more preferred embodiment of the present invention, the esterification reaction in step d) is performed in the presence of a treated bentonite catalyst, as defined above, in particular in the presence of an acid treated bentonite catalyst.

In a particular preferred embodiment of the present invention, the reaction in step c) and the esterification reaction in step d) are performed in the presence of the same treated bentonite catalyst, in particular in the presence of an acid treated bentonite catalyst.

Preferably, also in this particular embodiment, the treated bentonite catalyst used in steps c) and d) is separated from the reaction mixture after completion of the reaction in step d) and reused in a further reaction in step c), as describe above for step c).

In a special embodiment of the present invention, the reaction in steps c) and d) are conducted in the presence of at least one polar aprotic solvent (PS), as defined above; or in a solvent mixture consisting of at least one polar aprotic solvent (PS), as defined above, and at least one apolar hydrocarbon solvent (HS), as defined above.

In a more special embodiment of the present invention steps c) and d) are conducted in the presence of a carbonate solvent.

In another special embodiment of the present invention, the reaction in steps c) and d) are conducted in the presence of a carbonate solvent/apolar hydrocarbon solvent mixture, as described above.

Suitable and preferable carbonate solvents as well as suitable and preferable apolar hydrocarbon solvents (HS), if present, are as defined above.

Even more preferably, in this special embodiment, step d) is carried out in the same carbonate solvent and, if present, in the same apolar hydrocarbon solvents (HS), as applied in step c). In particular, the reaction mixture obtained in step c) is used directly in the reaction in step d), i.e. step c) and step d) are performed as a one-pot reaction.

The reaction product, i.e. the compound of formula (I), obtained in step d) can be worked up in a conventional way, e.g. by filtering off any solid catalyst, if present; by adding an apolar hydrocarbon solvent (HS), if necessary; separating the phases; and, where appropriate, purifying the crude products by using chromatographic methods, by distillation, if applicable, or by recrystallization.

In a special embodiment of the present invention, steps b), c) and d) are carried out in the same carbonate solvent and, if present, in the same apolar hydrocarbon solvent (HS). Preferably, in this special embodiment, the reaction mixture obtained in step b) is directly used in the reaction in step c), after removal of the hydrogenation catalyst, and the reaction mixture obtained in the subsequent step c) is directly used in the reaction in step d).

The process of the present invention provides the compounds (I) in high yields and selectivity. Typically, the compounds (I) are further purified by recrystallization, distillation, if applicable, or by using chromatographic methods.

Generally, only minor amounts of by-products are obtained.

Common by-products that are obtained by using processes described in the prior art for the preparation of compounds of the general formula (I), are for example diene compounds of the general formula X.1 to X.3, which are formed from compounds IV.a or IV.b via unwanted elimination reactions, as can be depicted from scheme 4.

Scheme 4:

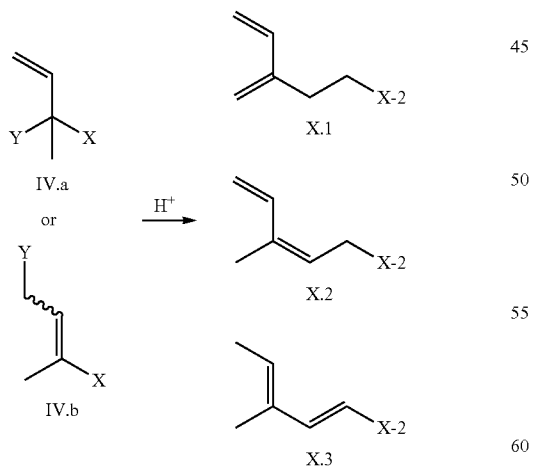

wherein
X is as defined above and
X-2 is preferably selected from moieties of formulae X-2.a and X-2.b

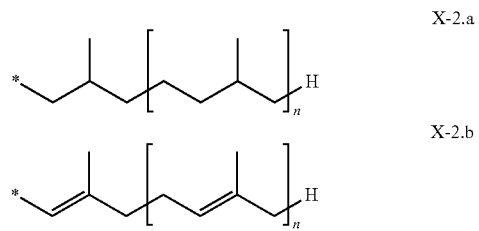

wherein
n is an integer of from 0 to 2 and
* indicates the attachment point to the rest of the molecule.

The formation of these diene by products is typically increased when carboxylic acids, such as oxalic acid, tartaric acid or citric acid, are applied as condensation catalysts. These acids are capable of forming ester intermediates with the compounds IV.a or IV.b., which can easily eliminate to the compounds of the general formula X.1 to X.3.

The diene compounds of the general formula X.1 to X.3 can also react with the compounds (III) in step c). However, the reaction is very slow compared to the reaction with compounds IV.a or IV.b. The formation of the diene compounds X.1 to X.3 should thus be avoided.

Furthermore, benzofurane isomers of formula XI-1 can be formed from the reaction of the hydroquinone compounds (III) with compounds IV.a, as depicted in scheme 5, which are difficult to separate from the desired compounds (I).

Scheme 5:

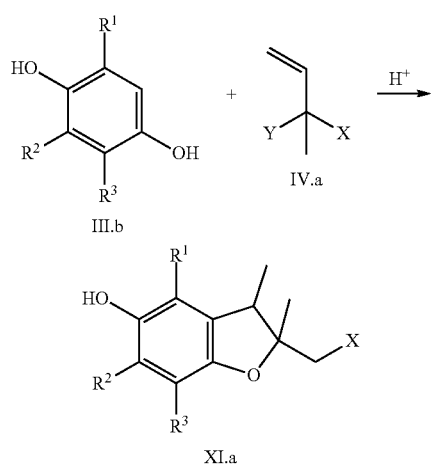

By using the process of the present invention, the formation of these common side products can successfully be suppressed.

The examples below provide further explanation of the invention. These examples are not to be understood as restricting the invention.

EXAMPLES

Abbreviations:
GC stands for gas chromatography,
HPLC high performance liquid chromatography,
TMH stands for trimethylhydroquinone (2,3,5-trimethylhydroquinone), TMQ stands for trimethylquinone (2,3,5-trimethylquinone),
PC propylene carbonate
EC ethylene carbonate
1. Analytics:
1.1 Determination of Product Purity:

The purity of the products was determined by Gas Chromatography area-%. The yield of the compounds I and II was determined via GC-weight-% using docosan as internal standard and n-heptane as solvent.

GC-system: Agilent 6980N;
GC-Column: Agilent DB-1: 30 m (length), 0.25 mm (inner diameter), 0.25 micrometer (film-thickness);
Temperature program: 80° C. to 350° C. at 10°/min, 350° C. for 10 minutes, total runtime: 37 minutes.

The amount of compounds (III) in the (final) reaction mixture was determined via HPLC-weight-%:
HPLC-System: Agilent Series 1200
HPLC-column: Zorbax Eclipse PAH, 1.8 μm, 50*4.6 mm von Agilent®
Eluent:
A: water with 0.1 vol-% $H_3PO_4$;
B: Acetonitril

| Time [min.] | % B |
| --- | --- |
| 0.0 | 5 |
| 3.0 | 15 |
| 10.0 | 100 |
| 17.0 | 100 |
| 17.1 | 5 |

Detector: UV-detector λ=210 nm, BW=5 nm, flow-rate: 1.2 mL/min, injection: 2 μL, Temperature: 60° C., run-time: 20 min., pressure: about 130 bar
1.2 Determination of the BET Surface Area:
System: Quantachrome Autosorb Automated Gas Sorption System 6B, serial-#: 10896010901;
Software: Autosorb for Windows® for AS-3 and AS-6 Version 1.22;
Sample weight: 0.28-0.43 g of solid catalyst (e.g. treated bentonite catalyst);
Bath temperature: 77.4 K;
Run time: 64-106.7 min;
Gas for measuring: nitrogen; Purity of gas: nitrogen 5.0;
Drying before measuring: via rotary vane pump and finally turbo-molecular pump for 16 hours at 120° C., <1 mbar;
System Parameters: Cross-Sec Area 16.2 Å/molec;
Multipoint BET: 5 points $p/p_o$; $0.05 \leq p/p_o \leq 0.30$.
1.3 Determination of the Residual Acidity of the Solid Catalyst (Mg KOH/g Solid Catalyst):

The determination of the residual acidity of the solid catalyst (e.g. treated bentonite catalyst) is conducted in such a way that first an aqueous suspension with a certain amount of the solid catalyst is prepared as follows: 1.0 g to 1.5 g of the solid catalyst is suspended in 50 mL of deionized water and stirred for 1 h. A previously calibrated KCl-pH-electrode is placed into this suspension. An aqueous NaOH solution with a defined concentration of 0.1 mol/L is then titrated to this aqueous suspension until the pH value of the suspension of the solid catalyst switches to the alkaline range (inflection point), which represents the end-point of the titration. The volume V1 in mL of NaOH solution used to reach the inflection point is recorded.

Furthermore, a blank determination is carried out in the same way using 50 mL of deionized water. The volume V2 in mL of NaOH solution used is recorded.

The residual acidity of the solid catalyst sample (in mg KOH/g solid catalyst), which is determined as total acid value, is then calculated based on the following formula:

$$\text{Residual acidity} = \frac{56.1 \frac{g}{mol} * (V1 - V2) * c * t}{m1}$$

56.1 g/mol represents a constant (molar mass of KOH in g/mol);
m1 is the mass, in grams, of the test portion, i.e. the solid catalyst sample;
V1 is the volume, in milliliters, of NaOH solution used to neutralize the catalyst suspension (volume until inflection point is reached);
V2 is the volume, in milliliters, of NaOH solution used in the blank determination (volume until inflection point is reached—usually no volume consumed/blank is typically zero);
C is the concentration, in moles per liter, of the NaOH solution;
t is the titer of the NaOH solution.

The determination of the residual acidity is repeated once and thus determined twice.
1.4 Determination of the Density of the Catalyst:
Machine: Pycnometer series AccuPyc II 1340
Company: Micromeritics
Inert gas: Helium
Sample weight: 2.1-4.8 g
Sample chamber: 10 mL
Program "analysis conditions" was used including 99 cycles and each cycle with 5 repetitions.
The samples were treated for 16 h at 120° C., <1 mbar vacuum before measuring.

Density [g/ccm]=mass of sample [g]/volume of sample [ccm]

1. Preparation Examples

Origin and Specification of the Applied Acid Treated Bentonite Catalysts

The acid treated bentonites that are used as catalysts in the following preparation examples are either acid treated bentonites from the company BASE SE that were developed in-house (BASE SE internal material) or acid treated Bentonites available from Sigma Aldrich or from the company Clariant Produkte GmbH.

Bentonite catalysts with the following specifications were applied:

| Catalyst No.: | Source: | Residual acidity [mg KOH/g] | Surface area (BET) [m²/g] | Water content *) [wt %] | He-density [g/ccm] |
| --- | --- | --- | --- | --- | --- |
| 1 | BASF SE | 30-36 | 215-235 | 12-16 | 2.57 ± 0.1 |
| 2 | BASF SE | 24-30 | 215-235 | 18-22 | 2.57 ± 0.1 |
| 3 | BASF SE | 26-32 | 300-320 | 11-15 | 2.45 ± 0.1 |
| 4 | BASF SE | 21-27 | 230-250 | 10-14 | 2.57 ± 0.1 |
| 5 | BASF SE | 16-22 | 275-295 | 11-15 | 2.56 ± 0.1 |
| 6 | Clariant Produkte GmbH | 18-24 | 145-165 | 10-14 | 2.39 ± 0.1 |

-continued

| Catalyst No.: | Source: | Residual acidity [mg KOH/g] | Surface area (BET) [m²/g] | Water content *) [wt %] | He-density [g/ccm] |
|---|---|---|---|---|---|
| 7 | Clariant Produkte GmbH | 11-17 | 265-285 | 9-13 | 2.46 ± 0.1 |
| 8 | Clariant Produkte GmbH | 13-19 | 285-305 | 10-14 | 2.45 ± 0.1 |
| 9 | Clariant Produkte GmbH | <1 | 175-195 | 8-12 | 2.46 ± 0.1 |

*) determined by Karl-Fischer-Titration and/or by weight loss on drying (16 h at 120° C. and at a pressure of <1 mbar).

For the preparation of the acid treated bentonite catalysts from the company BASF SE (catalysts 1 to 5) Aberdeen clay, which is known for its high quality, was used as the natural bentonite starting material. These bentonites are activated using sulfuric acid followed by conversion to the final granular mineral catalysts.

General Reaction Procedure and Remarks:

The reaction progress is monitored via thin layer chromatography and GC.

Step 1: Reduction of TMQ to TMH
Step 2: Friedel-Crafts-Alkylation and condensation Unless otherwise noted all reactions are performed in a glass flask using a blade agitator and a dean stark trap, which,
in case a mixture of HS and PS is used as the solvent, is filled with the HS employed,
in case a PS is used as the solvent that forms no azeotrope with water, is left empty, and
in case a solvent is used that forms an azeotrope with water, is filled with the solvent employed (unlike water) that is azeotropically removed with water.

Step 3: Esterification

2.1 Preparation of 2,3,5-trimethylhydroquinone (Step 1)

4 g 2,3,5-trimethylquinone (99.6%, 26.5 mmol) is dissolved in 76 g (63.1 mL) propylene carbonate at room temperature. 0.4 g palladium on charcoal (10%, 0.38 mmol, 0.01 eq) is added and the resulting reaction mixture is hydrogenated for 23 h at a hydrogen pressure of 8 bar and at 64° C. After a reaction time of 6 h the filtered reaction mixture is only a slightly yellowish solution, after a reaction time of 23 h a colorless solution. The following GC analysis is obtained:

| Reaction time [h] | GC-area-% | |
|---|---|---|
| | TMH | TMQ |
| 6 | 97.5 | 2.3 |
| 23 | 98.9 | 0.9 |

2.2 Preparation of 2,5,7,8-tetramethyl-2-[4,8,12-trimethyltridecyl]-3,4-dihydro-2H-chromen-6-ol (all racemic alpha-tocopherol) (Step 1 and 2)

Preparation of 2,3,5-trimethylhydroquinone 14 g 2,3,5-trimethylquinone (99.6%, 92.85 mmol) is dissolved in 79.3 g (65.9 mL) propylene carbonate at room temperature. 2.8 g palladium on charcoal (10%, 2.6 mmol, 0.03 eq) is added and the resulting reaction mixture is hydrogenated for 23 h at a hydrogen pressure of 8 bar and 88° C. Then, the reaction mixture is filtered immediately and 83.3 g of an almost colorless eluate (97.6 GC-a % TMH and 0.05 GC-a % TMQ) is obtained.

Preparation of all Racemic Alpha-Tocopherol (Catalyst 2):

Towards the crude TMH in propylene carbonate (81.4 g after analytics, assumption: 100% yield: 92.85 mmol, 1.7 eq) 0.19 g catalyst 2 (dried over night at 120° C./50 mbar in the vacuum drying oven)/g TMH (2.7 g catalyst 2) is added. The reaction mixture is brought to 120-125° C. and stirred for 15 min. Then, 16.45 g isophytol (97.4%, 54 mmol) is continuously added to the reaction mixture over a period of 2 h (temperature of the reaction mixture: 120-125° C.) while the water formed during the reaction is removed by distillation. After a further reaction time of 4 h at 125° C., at room temperature overnight, and further 4 h at 125° C. the reaction mixture is brought to room temperature, 20 mL of heptane is added, it was further stirred for 15 min and then filtered over celite to remove the catalyst 2. The filter cake is washed with 6*20 mL heptane and 3*20 mL propylene carbonate. After phase separation, the propylene carbonate phase is extracted with 4*25 mL heptane. The combined heptane phases are dried over sodium sulfate. The solvent is removed under reduced pressure 50° C./5 mbar plus 15 min oil pump vacuum. 24.09 g of crude alpha-tocopherol (91.6 GC-area % and 85.66 GC-weight %) is obtained as a dark red, clear, viscous residue in 89% yield (based on GC-weight % over two steps). Each step has an average yield of 94.5% yield.

2.3 Preparation of 2,5,7,8-tetramethyl-2-[4,8,12-trimethyltridecyl]-3,4-dihydro-2H-chromen-6-ol (all racemic alpha-tocopherol) (Step 2; Catalyst 1)

233.57 g (193.99 mL) propylene carbonate and 0.22 g catalyst 1 (dried at 120° C. overnight, 50 mbar)/g TMH (21.75 g catalyst 1) are heated under a nitrogen gas stream to 120-125° C. and stirred for 15 min. The suspension is then cooled to <90° C. and 100.11 g (652.5 mmol) trimethylhydroquinone (1.5 eq) is added. The mixture is then again heated to 120-125° C. Then, 136.35 g (162.13 mL) isophytol (447.9 mmol, 97.4% purity, 1 eq) is continuously added to the reaction mixture over a period of 2 h (temperature of the reaction mixture: 120-125° C.) while the water formed during the reaction is removed by distillation. After a further reaction time of 6 h at 120-125° C. the reaction mixture is cooled to room temperature. The mixture is filtered over a glass suction filter D4 loaded with celite to remove the catalyst 1. The filter cake is washed with 6*130 mL heptane and 3*130 mL propylene carbonate. All mother liquors and washing liquors are collected and joined. The phases of the eluate are separated. The propylene carbonate phase is extracted with 4*190 mL heptane. The combined heptane phases are dried over sodium sulfate and the volatiles are removed under reduced pressure at 50-55° C./5 mbar plus 15 min oil pump vacuum: 200 g of crude alpha-tocopherol (94.6 GC-area-% and 94.53 GC-weight-%) is obtained as dark red, clear, viscous residue. This corresponds to a yield of 98%.

2.4 Preparation of 2,5,7,8-tetramethyl-2-[4,8,12-trimethyltridecyl]-3,4-dihydro-2H-chromen-6-ol (all racemic alpha-tocopherol) (Step 2; Catalyst 1)

138.08 g (141.91 mL) diethyl carbonate and 0.22 g catalyst 1 (dried at 120° C. overnight, 50 mbar)/g TMH (7.5 g catalyst 1) are heated under a nitrogen gas stream to 120-123° C. and stirred for 15 min. The suspension is then cooled to <90° C. and 34.52 g (225 mmol) trimethylhydroquinone (1.5 eq) is added. The mixture is then again heated to 120-125° C. Then, 45.76 g (54.41 mL) isophytol (150 mmol, 97.2% purity, 1 eq) is continuously added to the reaction mixture over a period of 2 h (temperature of the reaction mixture: 124-119° C.) while the water formed during the reaction is removed by distillation. After a further reaction time of 6 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 1. The filter cake is washed with 6*45 mL heptane. All mother liquors and washing liquors are collected and joined. The eluate from which precipitation is observed is subsequently filtered and the solvent is removed under reduced pressure at 50-55° C./5 mbar plus 15 min oil pump vacuum: 68.84 g of crude alpha-tocopherol (84.8 GC-area-% and 78.79 GC-weight-%) is obtained as red-brown, viscous and cloudy residue. This corresponds to a yield of 84%.

2.5 Preparation of 2,5,7,8-tetramethyl-2-[4,8,12-trimethyltridecyl]-3,4-dihydro-2H-chromen-6-ol (all racemic alpha-tocopherol) (Step 2; Catalyst 1)

80.55 g (71.92 mL) gamma-butyrolactone and 0.22 g catalyst 1 (dried at 120° C. overnight, 50 mbar)/g TMH (7.5 g catalyst 1) are heated under a nitrogen gas stream to 120-125° C. and stirred for 15 min. The suspension is then cooled to <90° C. and 34.52 g (225 mmol) trimethylhydroquinone (1.5 eq) is added. The mixture is then again heated to 120-125° C. Then, 45.76 g (54.3 mL) isophytol (150 mmol, 97.4% purity, 1 eq) is continuously added to the reaction mixture over a period of 2 h (temperature of the reaction mixture: 120-125° C.) while the water formed during the reaction is removed by distillation. After a further reaction time of 6 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 1. The filter cake is washed with 6*45 mL heptane and 3*45 mL gamma-butyrolactone. All mother liquors and washing liquors are collected and joined. The phases of the eluate are separated. The gamma-butyrolactone phase is extracted with 4*65 mL heptane. The combined heptane phases are dried over sodium sulfate and the volatiles are removed under reduced pressure at 50-55° C./5 mbar plus 15 min oil pump vacuum: 68.71 g of crude alpha-tocopherol (89.7 GC-area-% and 78.38 GC-weight-%) is obtained as dark red, clear, viscous residue. This corresponds to a yield of 83%.

2.6 Preparation of 2,5,7,8-tetramethyl-2-[4,8,12-trimethyltridecyl]-3,4-dihydro-2H-chromen-6-ol (all racemic alpha-tocopherol) (Step 2; Catalyst 1)

This reaction was performed without water removal and thus a Dean stark trap. The apparatus used consists of a flask, blade agitator and reflux condenser. 80.55 g (66.9 mL) propylene carbonate and 0.22 g catalyst 1 (dried at 120° C. overnight, 50 mbar)/g TMH (7.5 g catalyst 1) are heated under a nitrogen gas stream to 120-125° C. and stirred for 15 min. The suspension is then cooled to <90° C. and 34.52 g (225 mmol) trimethylhydroquinone (1.5 eq) is added. The mixture is then again heated to 120-125° C. Then, 45.86 g (54.5 mL) isophytol (150 mmol, 97% purity, 1 eq) is continuously added to the reaction mixture over a period of 2 h (temperature of the reaction mixture: 120-125° C.). After a further reaction time of 4 h at 123-124° C., at room temperature overnight, and further 2 h at 124° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 1. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50-55° C./5 mbar plus 15 min oil pump vacuum: 66.04 g of crude alpha-tocopherol (92.7 GC-area-% and 84.55 GC-weight-%) is obtained as dark red, clear, viscous residue. This corresponds to a yield of 86%.

2.7 Preparation of 2,5,7,8-tetramethyl-2-[4,8,12-trimethyltridecyl]-3,4-dihydro-2H-chromen-6-ol (all racemic alpha-tocopherol) (Step 2; Catalyst 2)

103.14 g (78.08 mL) ethylene carbonate, 47.73 g (67.9 mL) n-octane (plus 60 mL octane in dean-stark-trap) and 0.65 g catalyst 2 (dried at 120° C. overnight, 50 mbar)/g TMH (22.5 g catalyst 2) are heated under a nitrogen gas stream to slight n-octane reflux (temperature of the reaction mixture: 120-125° C.) and stirred for 15 min under reflux. The suspension is then cooled to <80° C. and 34.38 g (225 mmol) trimethylhydroquinone (1.5 eq) is added. The mixture is then again heated to 120° C. Then, 45.39 g (53.97 mL) isophytol (150 mmol, 98% purity, 1 eq) is continuously added to the reaction mixture over a period of 2 h (temperature of the reaction mixture: 120-125° C.) while the water formed during the reaction is removed by distillation. After a further reaction time of 6 h at 123-126° C. the reaction mixture is cooled to <60° C. and 50 g of propylene carbonate is added. Then, the reaction mixture is further cooled to room temperature and filtered over a glass suction filter D4 loaded with celite to remove the catalyst 2. The filter cake is washed with 3*45 mL octane and 3*45 mL propylene carbonate. All mother liquors and washing liquors are collected and joined. The phases of the eluate are separated. The ethylene/propylene carbonate phase is extracted with 4*65 mL octane. The combined octane phases are dried over sodium sulfate and the volatiles are removed under reduced pressure at 50-55° C./5 mbar plus 15 min oil pump vacuum: 63.66 g of crude alpha-tocopherol (95.5 GC-area-% and 91.44 GC-weight-%) is obtained as dark red, clear, viscous residue. This corresponds to a yield of 90%.

2.8 Preparation of 2,5,7,8-tetramethyl-2-[4,8,12-trimethyltridecyl]-3,4-dihydro-2H-chromen-6-ol (all racemic alpha-tocopherol) (Step 2; Catalyst 2)

232.63 g (193.21 mL) propylene carbonate, 118.06 g (167.9 mL) n-octane (plus 60 mL octane in dean-stark-trap) and 0.22 g catalyst 2 (dried at 120° C. overnight, 50 mbar)/g TMH (21.75 g catalyst 2) are heated under a nitrogen gas stream to slight n-octane reflux (temperature of the reaction mixture: 120-125° C.) and stirred for 15 min under reflux. The suspension is then cooled to <80° C. and 99.7 g (625.5 mmol) trimethylhydroquinone (1.5 eq) is added. The mixture is then again heated to 123° C. Then, 137.22 g (163.17 mL) isophytol (435 mmol, 94% purity, 1 eq) is continuously added to the reaction mixture over a period of 2 h (temperature of the reaction mixture: 125-123° C.) while the water formed during the reaction is removed by distillation. After a further reaction time of 4 h at 123-125° C., at room temperature overnight, and further 2 h at 125° C. the reaction mixture is cooled to room temperature and filtered over a glass suction filter D4 loaded with celite to remove the catalyst 2. The filter cake is washed with 3*130 mL heptane and 3*130 mL propylene carbonate. All mother liquors and washing liquors are collected and joined. The phases of the eluate are separated. The propylene carbonate phase is extracted with 4*190 mL heptane. The combined heptane/n-octane phases are dried over sodium sulfate and the volatiles are removed under reduced pressure at 50-55° C./5 mbar plus 15 min oil pump vacuum: 199.16 g of crude alpha-tocopherol (92.6 GC-area-% and 87.57 GC-weight-%) is obtained as dark red, clear, viscous residue. This corresponds to a yield of 93%.

2.9 Preparation of 2,5,7,8-tetramethyl-2-[4,8,12-trimethyltridecyl]-3,4-dihydro-2H-chromen-6-ol (all racemic alpha-tocopherol) (Step 2; Catalyst 2)

80.55 g (66.9 mL) propylene carbonate and 0.22 g catalyst 2 (dried at 120° C. overnight, 50 mbar)/g TMH (7.5 g catalyst 2) are heated to 50-90° C. and 34.52 g (225 mmol) trimethylhydroquinone (1.5 eq) is added. The mixture is then heated to 150° C. and 45.67 g (54.3 mL) isophytol (150 mmol, 97.4% purity, 1 eq) is continuously added to the reaction mixture over a period of 2 h. After a further reaction time of 6 h the reaction mixture is cooled to room temperature. 45 mL of heptane is added to the reaction mixture which is stirred for 15 min at room temperature. Then, the mixture is filtered over a glass suction filter D4 loaded with celite to remove the catalyst 2. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 65.61 g of crude alpha-tocopherol (92.5 GC-area-% and 84.73 GC-weight-%) is obtained as dark red, clear, viscous residue. This corresponds to a yield of 86%.

2.10 Preparation of 2,5,7,8-tetramethyl-2-[4,8,12-trimethyltridecyl]-3,4-dihydro-2/H chromen-6-ol (all racemic alpha-tocopherol) (Step 2; Catalyst 2)

80.55 g (66.9 mL) propylene carbonate and 0.33 g catalyst 2 (dried at 120° C. overnight, 50 mbar)/g TMH (11.25 g catalyst 2) are heated under a nitrogen gas stream to 120-125° C. and stirred for 15 min. The suspension is then cooled to <90° C. and 34.52 g (225 mmol) trimethylhydroquinone (3 eq) is added. The mixture is then again heated to 120-125° C. Then, 22.88 g (27.21 mL) isophytol (75 mmol, 97.2% purity, 1 eq) is continuously added to the reaction mixture over a period of 1 h (temperature of the reaction mixture: 121-125° C.). After a further reaction time of 6 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 2. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 33.99 g of crude alpha-tocopherol (95.2 GC-area-% and 88.45 GC-weight-%) is obtained as dark red, clear, viscous residue. This corresponds to a yield of 93%.

2.11 Preparation of 2,5,7,8-tetramethyl-2-[4,8,12-trimethyltridecyl]-3,4-dihydro-2H-chromen-6-ol (all racemic alpha-tocopherol) (Step 2; Catalyst 2)

80.55 g (66.9 mL) propylene carbonate, 39.79 g (58.18 mL) n-heptane (plus 60 mL heptane in dean-stark-trap) and 0.22 g catalyst 2 (dried at 120° C. overnight, 50 mbar)/g TMH (7.5 g catalyst 2) are heated under a nitrogen gas stream to slight n-heptane reflux (temperature of the reaction mixture: 100° C.) and stirred for 15 min under reflux. The suspension is then cooled to <80° C. and 34.52 g (225 mmol) trimethylhydroquinone (1.5 eq) is added. The mixture is then again heated to 100° C. Then, 45.86 g (54.52 mL) isophytol (150 mmol, 97% purity, 1 eq) is continuously added to the reaction mixture over a period of 2 h (temperature of the reaction mixture: 100-102° C.) while the water formed during the reaction is removed by distillation. After a further reaction time of 6 h at 103-104° C., at room temperature overnight, and further 2 h at 102° C. the reaction mixture is cooled to room temperature and filtered over a glass suction filter D4 loaded with celite to remove the catalyst 2. The filter cake is washed with 3*45 mL heptane and 3*45 mL propylene carbonate. All mother liquors and washing liquors are collected and joined. The phases of the eluate are separated. The propylene carbonate phase is extracted with 4*65 mL heptane. The combined heptane/n-octane phases are dried over sodium sulfate and the volatiles are removed under reduced pressure at 50° C./5 mbar plus 15 min oil pump vacuum: 63.99 g of crude alpha-tocopherol (88.9 GC-area-% and 85.26 GC-weight-%) is obtained as dark red, clear, viscous residue. This corresponds to a yield of 84%.

2.12 Preparation of 2,5,7,8-tetramethyl-2-[4,8,12-trimethyltridecyl]-3,4-dihydro-2/H-chromen-6-ol (all racemic alpha-tocopherol) (Step 2; Catalyst 3)

80.55 g (66.9 mL) propylene carbonate and 0.22 g catalyst 3 (dried at 120° C. overnight, 50 mbar)/g TMH (7.5 g catalyst 3) are heated under a nitrogen gas stream to 120-125° C. and stirred for 15 min. The suspension is then cooled to <90° C. and 34.52 g (225 mmol) trimethylhydroquinone (1.5 eq) is added. The mixture is then again heated to 120-125° C. Then, 45.86 g (54.52 mL) isophytol (150 mmol, 97% purity, 1 eq) is continuously added to the reaction mixture over a period of 2 h (temperature of the reaction mixture: 122-125° C.). After a further reaction time of 4 h at 120-125° C., at room temperature over the weekend, and further 2 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 3. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 65.43 g of crude alpha-tocopherol (94.1 GC-area-% and 87.05 GC-weight-%) is obtained as dark red, clear, viscous residue. This corresponds to a yield of 88%.

2.13 Preparation of 2,5,7,8-tetramethyl-2-[4,8,12-trimethyltridecyl]-3,4-dihydro-2H-chromen-6-ol (all racemic alpha-tocopherol) (Step 2; Catalyst 4)

80.22 g (66.63 mL) propylene carbonate, 40.71 g (57.91 mL) n-octane (plus 60 mL octane in dean-stark-trap) and 0.65 g catalyst 4 (dried at 120° C. overnight, 50 mbar)/g TMH (22.5 g catalyst 4) are heated under a nitrogen gas stream to slight n-octane reflux (temperature of the reaction mixture: 120-122° C.) and stirred for 15 min under reflux. The suspension is then cooled to <80° C. and 34.38 g (225 mmol) trimethylhydroquinone (1.5 eq) is added. The mixture is then again heated to 120° C. Then, 45.39 g (53.97 mL) isophytol (150 mmol, 98% purity, 1 eq) is continuously added to the reaction mixture over a period of 2 h (temperature of the reaction mixture: 118-120° C.) while the water formed during the reaction is removed by distillation. After a further reaction time of 6 h at 121-124° C. the reaction mixture is cooled to room temperature and filtered over a glass suction filter D4 loaded with celite to remove the catalyst 4. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 64.06 g of crude alpha-tocopherol (90.5 GC-area-% and 86.86 GC-weight-%) is obtained as dark red, clear, viscous residue. This corresponds to a yield of 86%.

2.14 Preparation of 2,5,7,8-tetramethyl-2-[4,8,12-trimethyltridecyl]-3,4-dihydro-2/H-chromen-6-ol (all racemic alpha-tocopherol) (Step 2; Catalyst 5)

80.22 g (66.63 mL) propylene carbonate, 40.71 g (57.91 mL) n-octane (plus 60 mL octane in dean-stark-trap) and 0.65 g catalyst 5 (dried at 120° C. overnight, 50 mbar)/g TMH (22.5 g catalyst 5) are heated under a nitrogen gas stream to slight n-octane reflux (temperature of the reaction mixture: 120-121° C.) and stirred for 15 min under reflux. The suspension is then cooled to <80° C. and 34.38 g (225 mmol) trimethylhydroquinone (1.5 eq) is added. The mixture is then again heated to 120° C. Then, 45.39 g (53.97 mL) isophytol (150 mmol, 98% purity, 1 eq) is continuously added to the reaction mixture over a period of 2 h (temperature of the reaction mixture: 115-120° C.) while the water formed during the reaction is removed by distillation. After a further reaction time of 4 h at 119-123° C., at room temperature over the weekend, and further 2 h at 122° C. the reaction mixture is cooled to room temperature and filtered over a glass suction filter D4 loaded with celite to remove the catalyst 5. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 65.08 g of crude alpha-tocopherol (87.3 GC-area-% and 85.15 GC-weight-%) is obtained as dark red, clear, viscous residue. This corresponds to a yield of 86%.

2.15 Preparation of 2,5,7,8-tetramethyl-2-[4,8,12-trimethyltridecyl]-3,4-dihydro-2/H-chromen-6-ol (all racemic alpha-tocopherol) (Step 2; Catalyst 6)

80.55 g (66.9 mL) propylene carbonate and 0.33 g catalyst 6 (undried)/g TMH (11.25 g catalyst 6) are heated under a nitrogen gas stream to 120-125° C. and stirred for 15 min. The suspension is then cooled to <90° C. and 34.52 g (225 mmol) trimethylhydroquinone (1.5 eq) is added. The mixture is then again heated to 120-125° C. Then, 45.67 g (54.3 mL) isophytol (150 mmol, 97.4% purity, 1 eq) is continuously added to the reaction mixture over a period of 1 h (temperature of the reaction mixture: 122-125° C.). After a further reaction time of 6 h at 122-125° C. the reaction mixture is cooled to room temperature. 45 mL of heptane and celite is added to the reaction mixture which is stirred for 15 min at room temperature. Then, the mixture is filtered over a glass suction filter D4 to remove celite and catalyst 6. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 64.75 g of crude alpha-tocopherol (86.7 GC-area-% and 81.19 GC-weight-%) is obtained as dark red, clear, viscous residue. This corresponds to a yield of 81%.

2.16 Preparation of 2,5,7,8-tetramethyl-2-[4,8,12-trimethyltridecyl]-3,4-dihydro-2H-chromen-6-ol (all racemic alpha-tocopherol) (Step 2; Catalyst 7)

80.55 g (66.9 mL) propylene carbonate and 0.33 g catalyst 7 (undried)/g TMH (11.25 g catalyst 7) are heated under a nitrogen gas stream to 120-122° C. and stirred for 15 min. The suspension is then cooled to <90° C. and 34.52 g (225 mmol) trimethylhydroquinone (1.5 eq) is added. The mixture is then again heated to 120-125° C. Then, 45.67 g (54.3 mL) isophytol (150 mmol, 97.4% purity, 1 eq) is continuously added to the reaction mixture over a period of 1 h (temperature of the reaction mixture: 120-124° C.). After a further reaction time of 6 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 7. The filter cake is washed with 6*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 64.76 g of crude alpha-tocopherol (91.8 GC-area-% and 86.01 GC-weight-%) is obtained as dark red, clear, viscous residue. This corresponds to a yield of 86%.

2.17 Preparation of 2,5,7,8-tetramethyl-2-[4,8,12-trimethyltridecyl]-3,4-dihydro-2H-chromen-6-ol (all racemic alpha-tocopherol) (Step 2; Catalyst 8)

80.55 g (66.9 mL) propylene carbonate and 0.44 g catalyst 8 (undried)/g TMH (15 g catalyst 8) are heated under a nitrogen gas stream to 120° C. and stirred for 15 min. The suspension is then cooled to <90° C. and 34.52 g (225 mmol) trimethylhydroquinone (1.5 eq) is added. The mixture is then again heated to 120-125° C. Then, 45.67 g (54.3 mL) isophytol (150 mmol, 97.4% purity, 1 eq) is continuously added to the reaction mixture over a period of 2 h (temperature of the reaction mixture: 121-125° C.). After a further reaction time of 4 h at 121-125° C., room temperature overnight, and further 2 h at 120-125° C. the reaction mixture is cooled to room temperature. 45 mL of heptane is added to the reaction mixture which is stirred for 15 min at room temperature. Then, the mixture is filtered over a glass suction filter D4 loaded with celite to remove the catalyst 8. The filter cake is washed with 6*45 mL heptane and 4*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 64.27 g of crude alpha-tocopherol (75.8 GC-area-% and 87.13 GC-weight-%) is obtained as dark red, clear, viscous residue. This corresponds to a yield of 87%.

2.18 Preparation of 2,5,7,8-tetramethyl-2-[4,8,12-trimethyltridecyl]-3,4-dihydro-2H-chromen-6-ol (all racemic alpha-tocopherol) (Step 2; Catalyst 9)

80.55 g (66.9 mL) propylene carbonate and 0.33 g catalyst 9 (undried)/g TMH (11.25 g catalyst 9) are heated under a nitrogen gas stream to 120° C. and stirred for 15 min. The suspension is then cooled to <90° C. and 34.52 g (225 mmol) trimethylhydroquinone (1.5 eq) is added. The mixture is then again heated to 120-125° C. Then, 45.67 g (54.3 mL) isophytol (150 mmol, 97.4% purity, 1 eq) is continuously added to the reaction mixture over a period of 1 h (temperature of the reaction mixture: 123-125° C.). After a further reaction time of 6 h at 125° C. the reaction mixture is analysed: 30 GC-area % TMH, 5 GC-area % phytadienes, 19 GC-area % Phytyl-TMH, no alpha-tocopherol. The reaction mixture is discarded.

2.19 Continuous preparation of 2,5,7,8-tetramethyl-2-[4,8,12-trimethyltridecyl]-3,4-dihydro-2H-chromen-6-ol (all racemic alpha-tocopherol) (Step 2; Catalyst 9)

Applied Catalyst:
Montmorillonite K10 (pH of 3-4, surface area) "diluted" with Celite in a 1:1 mass ratio from the company Thales Nano, packed into a cartridge (so-called CatCart). The employed CatCart-cartridge had a size of 70×4 mm and a filling mass of 459 mg.
Continuous Preparation Procedure:
An 8 wt % solution of TMH in bis(2-methoxyethyl)ether (=diglyme) and a 10.4 wt % solution of isophytol in bis(2-methoxyethyl)ether (=diglyme) are pumped with a volume flow of 5 mL/h onto the above described CatCart filled with K10 and Celite and heated to 200° C. The catalyst CatCart is placed in vertical position.
The reaction progress is monitored via GC: 61.3 GC-area % of 2,5,7,8-tetramethyl-2-[4,8,12-trimethyltridecyl]-3,4-dihydro-2H-chromen-6-ol (all racemic alpha-tocopherol), 19.4 GC-area % of TMH and 13.5 GC-area % of phytadienes are obtained.

2.20 Preparation of all Racemic Alpha-Tocopherol Acetate (Steps 1, 2 and 3)

Preparation of 2,3,5-trimethylhydroquinone
14 g 2,3,5-trimethylquinone (99.6%, 92.85 mmol) is dissolved in 79.7 g (66.2 mL) propylene carbonate at room temperature. 2.8 g palladium on charcoal (10%, 2.63 mmol, 0.03 eq) is added and the resulting reaction mixture is hydrogenated for 22.5 h at a hydrogen pressure of 8 bar and at 87-93° C. The reaction mixture is filtered at temperature and under nitrogen using a warm glass suction filter D4 with a paper filter and 84.31 g eluate (95.3 GC-area % trimethylhydroquinone and 0.28 GC-a % trimethylquinone) are obtained.
Preparation of all Racemic Alpha-Tocopherol (Catalyst 2)
Towards the crude trimethylhydroquinone in propylene carbonate obtained in the first step (82.83 g, 1.73 eq, assumption 100% yield, 92.85 mmol) 0.19 g catalyst 2 (dried at 120° C. overnight, 50 mbar)/g TMH (2.69 g catalyst 2) are added and heated to 120° C. and stirred for 15 min at 120-124° C. Then, 16.38 g (19.47 mL) isophytol (53.8 mmol, 97.4% purity, 1 eq) is continuously added to the reaction mixture over a period of 2 h (temperature of the reaction mixture: 124-125° C.) while the water formed during the reaction is removed by distillation. After a further reaction time of 5 h at 125° C. the reaction mixture is stirred overnight at room temperature.
Preparation of all Racemic Alpha-Tocopherol Acetate (Catalyst 2)
The brown suspension obtained from the second step is heated to 50° C. and 22.19 g (20.55 mL) acetic anhydride (220 mmol, 4 eq) are continuously added over a period of 15 min. Then, the reaction mixture is heated to 100° C. and stirred for 4 h. After cooling to room temperature, 20 mL of heptane is added to the reaction mixture which is stirred for 15 min. Then, the reaction mixture is filtered over a glass suction filter D4 loaded with celite to remove the catalyst 2. The filter cake is washed with 6*20 mL heptane and 3*20 mL propylene carbonate. All mother liquors and washing liquors are collected and joined. The phases of the eluate are separated. The propylene carbonate phase is extracted with 4*25 mL heptane. The combined heptane phases are dried over sodium sulfate and the volatiles are removed under reduced pressure at 50° C./5 mbar plus 15 min oil pump vacuum: 25.71 g of crude all racemic alpha-tocopherol acetate (89.28 GC-area-%) is obtained as brown, clear, viscous residue. This corresponds to a yield of 90% (based on GC-area % over 3 steps).

2.21 Preparation of all Racemic Alpha-Tocopherol Acetate (Steps 2 and 3)

Preparation of all Racemic Alpha-Tocopherol (Catalyst 2)
100.29 g (83.3 mL) propylene carbonate and 35.15 g catalyst 2 are added and heated to 120-125° C. and stirred for 15 min. The suspension is then cooled to <90° C. and 22.92 g (150 mmol) trimethylhydroquinone (1.0 eq) is added. The mixture is then again heated to 120° C. Then, 46.75 g (55.59 mL) isophytol (154.5 mmol, 98% purity, 1.03 eq) is continuously added to the reaction mixture over a period of 2 h (temperature of the reaction mixture: 120-123° C.) while the water formed during the reaction is removed by distillation. After a further reaction time of 4 h at 123-124° C. the reaction mixture is stirred over the weekend at room temperature.

Preparation of all Racemic Alpha-Tocopherol Acetate (Catalyst 2)

Towards the brown suspension obtained from the previous step 30.94 g (28.64 mL) acetic anhydride (300 mmol, 2 eq) are continuously added over a period of 10 min. Then, the reaction mixture is reactively distilled for 2 h (500 mbar, inner temperature 87-92° C., transition temperature 28-33° C., oil bath temperature 100° C.). Then, the reaction mixture is brought to room temperature and 45 mL of heptane is added and the reaction mixture is stirred for 15 min. Then, it is filtered over a glass suction filter D4 to remove the catalyst 2. The filter cake is washed with 3*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 71.79 g of crude all racemic alpha-tocopherol acetate (88.08 GC-area-%) is obtained as brown, clear, viscous residue containing 0.18 GC-area % alpha-tocopherol. This corresponds to a yield of 89% (based on GC-area % over 2 steps).

2.22 Effect of the Drying Temperature of the Bentonite Catalyst

The effect of drying the bentonite catalyst prior to its use in the condensation reaction of TMH with IP was evaluated. Two reactions were conducted in analogy to example 2.8, except that 225 mmol TMH were applied here instead of 625.5 mmol TMH (the amounts of the other reactants were adapted accordingly). The results are summarized in table 1.

TABLE 1

Influence of the drying temperature of the bentonite catalyst 2 on alpha-tocopherol yield

| Example No: | Entry: | Drying temperature catalyst 2 [° C.] | alpha-tocopherol yield [%] |
|---|---|---|---|
| 2.22.1. | 1 | undried | 79 |
| 2.22.2. | 2 | 60 | 82 |
| 2.22.3. | 3 | 100 | 88 |
| 2.22.4 | 4 | 120 | 93 |

In the bentonite catalyzed reaction of TMH with IP, the drying of the bentonite catalyst prior to its use can improve the catalyst turnover under the reaction conditions applied here (e.g. the applied PC/octane solvent mixture).

The yield of alpha-tocopherol increases with increasing drying temperature of the bentonite catalyst 2 from 79% (undried catalyst 2) to 93% (catalyst 2 dried at 120° C., 50 mbar, vacuum drying oven, overnight).

Example 2.22.1

Preparation of all Racemic Alpha-Tocopherol 80.22 g (66.6 mL) propylene carbonate, 40.71 g (57.91 mL) n-octane (plus 60 mL octane in dean-stark-trap) and 0.74 g catalyst 2 (undried as it is)/g TMH (25.43 g catalyst 2) are heated under a nitrogen gas stream to slight reflux (temperature of the reaction mixture: 109° C.) and stirred for 15 min under reflux. The suspension is then cooled to <80° C. and 34.38 g (225 mmol) trimethylhydroquinone (1.5 eq) is added. The mixture is then again heated to slight reflux at 113° C. Then, 45.39 g (53.97 mL) isophytol (150 mmol, 98% purity, 1 eq) is continuously added to the reaction mixture over a period of 2 h (temperature of the reaction mixture: 113-112° C.) while the water formed during the reaction is removed by distillation. After a further reaction time of 6 h at 118-123° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 59.31 g of crude alpha-tocopherol (89.7 GC-area-% and 85.47 GC-weight-%) is obtained as dark red, clear, viscous residue. This corresponds to a yield of 79%.

Example 2.22.2

Preparation of all Racemic Alpha-Tocopherol 80.22 g (66.6 mL) propylene carbonate, 40.71 g (57.91 mL) n-octane (plus 60 mL octane in dean-stark-trap) and 0.65 g catalyst 2 (dried at 60° C., overnight, 50 mbar)/g TMH (22.5 g catalyst 2) are heated under a nitrogen gas stream to slight reflux (temperature of the reaction mixture: 115-117° C.) and stirred for 15 min under reflux. The suspension is then cooled to <80° C. and 34.38 g (225 mmol) trimethylhydroquinone (1.5 eq) is added. The mixture is then again heated to slight reflux at 118° C. Then, 45.39 g (53.97 mL) isophytol (150 mmol, 98% purity, 1 eq) is continuously added to the reaction mixture over a period of 2 h (temperature of the reaction mixture: 119-117° C.) while the water formed during the reaction is removed by distillation. After a further reaction time of 6 h at 120-124° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 61.10 g of crude alpha-tocopherol (91.1 GC-area-% and 86.31 GC-weight-%) is obtained as dark red, clear, viscous residue. This corresponds to a yield of 82%.

Example 2.22.3

Preparation of all Racemic Alpha-Tocopherol 80.22 g (66.6 mL) propylene carbonate, 40.71 g (57.91 mL) n-octane (plus 60 mL octane in dean-stark-trap) and 0.65 g catalyst 2 (dried at 100° C., overnight, 50 mbar)/g TMH (22.5 g catalyst 2) are heated under a nitrogen gas stream to slight reflux (temperature of the reaction mixture: 120-121° C.) and stirred for 15 min under reflux. The suspension is then cooled to <80° C. and 34.38 g (225 mmol) trimethylhydroquinone (1.5 eq) is added. The mixture is then again heated to slight reflux at 122° C. Then, 45.39 g (53.97 mL) isophytol (150 mmol, 98% purity, 1 eq) is continuously added to the reaction mixture over a period of 2 h (temperature of the reaction mixture: 122-121° C.) while the water formed during the reaction is removed by distillation. After a further reaction time of 6 h at 123-125° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 65.91 g of crude alpha-tocopherol (92.1 GC-area-% and 86.47 GC-weight-%) is obtained as dark red, clear, viscous residue. This corresponds to a yield of 88%.

Example 2.22.4

Preparation of all Racemic Alpha-Tocopherol 80.22 g (66.6 mL) propylene carbonate, 40.71 g (57.91 mL) n-octane (plus 60 mL octane in dean-stark-trap) and 0.65 g catalyst 2 (dried at 120° C., overnight, 50 mbar)/g TMH (22.5 g catalyst 2) are heated under a nitrogen gas stream to slight reflux (temperature of the reaction mixture: 120-121° C.) and stirred for 15 min under reflux. The suspension is then cooled to <80° C. and 34.38 g (225 mmol) trimethylhydroquinone (1.5 eq) is added. The mixture is then again heated to slight reflux at 121° C. Then, 45.39 g (53.97 mL) isophytol (150 mmol, 98% purity, 1 eq) is continuously added to the reaction mixture over a period of 2 h (temperature of the reaction mixture: 115-121° C.) while the water formed during the reaction is removed by distillation. After a further reaction time of 6 h at 118-123° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 68.47 g of crude alpha-tocopherol (91.2 GC-area-% and 87.93 GC-weight-%) is obtained as dark red, clear, viscous residue. This corresponds to a yield of 93%.

2.23 Recycling of the Bentonite Catalyst in Step 2

The possibility to recycle the bentonite catalyst applied in the Friedel-Crafts-alkylation and condensation reaction was evaluated. Several reactions were conducted as described below (example 2.23.1), in which the bentonite catalyst 2 was recovered in each reaction and reused in the following identical reaction.

The recycling of the bentonite catalyst 2 was shown fivefold for the Friedel-Crafts-alkylation and condensation reaction under otherwise identical conditions (see examples 2.23.1. to 2.23.6. in Table 2). The yield can be reproduced within the scope of the error.

TABLE 2

Recycling of the bentonite catalyst 2

| Example No: | Entry: | alpha-Tocopherol yield [%] |
|---|---|---|
| 2.23.1. | 1 | 86 |
| 2.23.2. | 2 | 87 |
| 2.23.3. | 3 | 89 |
| 2.23.4. | 4 | 87 |
| 2.23.5. | 5 | 90 |
| 2.23.6. | 6 | 89 |

Example 2.23.1

Preparation of all Racemic Alpha-Tocopherol 80.22 g (66.63 mL) propylene carbonate, 40.71 g (57.91 mL) n-octane (plus 60 mL octane in dean-stark-trap) and 0.65 g catalyst 2 (dried at 120° C., overnight, 50 mbar)/g TMH (22.5 g catalyst 2) are heated under a nitrogen gas stream to slight n-octane reflux (temperature of the reaction mixture: 120-121° C.) and stirred for 15 min under reflux. The suspension is then cooled to <80° C. and 34.38 g (225 mmol) trimethylhydroquinone (1.5 eq) is added. The mixture is then again heated to 121° C. Then, 45.39 g (53.97 mL) isophytol (150 mmol, 98% purity, 1 eq) is continuously added to the reaction mixture over a period of 2 h (temperature of the reaction mixture: 116-121° C.) while the water formed during the reaction is removed by distillation. After a further reaction time of 4 h at 120-122° C., at room temperature overnight, and further 2 h at 122° C. the reaction mixture is cooled to room temperature and filtered over a glass suction filter D4 to remove the catalyst 2. The filter cake is washed with 3*45 mL n-octane and 3*45 mL propylene carbonate. The residue is sucked to dryness and further dried in a stream of nitrogen overnight (moist weight: 40.20 g, dry weight: 38.11 g). The thus recycled bentonite catalyst 2 is again applied in example 2.23.2.

All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 64.90 g of crude alpha-tocopherol (92.0 GC-area-% and 86.02 GC-weight-%) is obtained as red, clear, viscous residue. This corresponds to a yield of 86%.

Example 2.23.2

Preparation of all Racemic Alpha-Tocopherol 80.22 g (66.63 mL) propylene carbonate, 40.71 g (57.91 mL) n-octane (plus 60 mL octane in dean-stark-trap) and 38.11 g catalyst 2 from example 2.23.1. are heated under a nitrogen gas stream to slight n-octane reflux (temperature of the reaction mixture: 120-124° C.) and stirred for 15 min under reflux. The suspension is then cooled to <80° C. and 34.38 g (225 mmol) trimethylhydroquinone (1.5 eq) is added. The mixture is then again heated to 122° C. Then, 45.39 g (53.97 mL) isophytol (150 mmol, 98% purity, 1 eq) is continuously added to the reaction mixture over a period of 2 h (temperature of the reaction mixture: 119-122° C.) while the water formed during the reaction is removed by distillation. After a further reaction time of 2 h at 122° C., at room temperature overnight, and further 4 h at 123-124° C. the reaction mixture is cooled to room temperature and filtered over a glass suction filter D4 to remove the catalyst 2. The filter cake is washed with 3*45 mL n-octane and 3*45 mL propylene carbonate. The residue is sucked to dryness and further dried in a stream of nitrogen over the weekend (dry weight: 33.33 g). The thus recycled bentonite catalyst 2 is again applied in example 2.23.3.

All mother liquors and washing liquors are collected and joined. The phases of the eluate are separated. The propylene carbonate phase is extracted with 4*65 mL heptane. The combined heptane/n-octane phases are dried over sodium sulfate and the volatiles are removed under reduced pressure at 55° C./5 mbar plus 15 min oil pump vacuum: 65.62 g of crude alpha-tocopherol (92.6 GC-area-% and 86.04 GC-weight-%) is obtained as red, clear, viscous residue. This corresponds to a yield of 87%.

Examples 2.23.3-2.23.6 are performed as described in Example 2.23.2.

2.24 Recycling of the Bentonite Catalyst in Step 2 and 3

Example 2.24.1

Preparation of all Racemic Alpha-Tocopherol 100.29 g (83.3 mL) propylene carbonate and 1.01 g catalyst 2 (dried at 120° C., overnight, 50 mbar)/g TMH (23.17 g catalyst 2) are added and heated to 123-124° C. and stirred for 15 min. The suspension is then cooled to <90° C. and 22.92 g (150 mmol) trimethylhydroquinone (1.0 eq) is added. The mixture is then again heated to 120° C. Then, 46.75 g (55.59 mL) isophytol (154.5 mmol, 98% purity, 1.03 eq) is continuously added to the reaction mixture over a period of 2 h (temperature of the reaction mixture: 120-121° C.) while the water formed during the reaction is removed by distillation. After a further reaction time of 4 h at 120-125° C. the reaction mixture is stirred overnight at room temperature.

Preparation of all Racemic Alpha-Tocopherol Acetate

Towards the brown suspension obtained from the previous step 30.94 g (28.64 mL) acetic anhydride (300 mmol, 2 eq) are continuously added over a period of 10 min. Then, the reaction mixture is reactively distilled for 1 h (310-335 mbar, inner temperature 74-88° C., transition temperature 28-45° C., oil bath temperature 100° C.). The reaction mixture is stirred at room temperature under normal pressure over the weekend. Then, the reaction mixture is further reactively distilled for 1 h (310-335 mbar, inner temperature 64-67° C., transition temperature 32-34° C., oil bath temperature 75° C.). Then, the reaction mixture is brought to room temperature and 45 mL of heptane is added and the reaction mixture is stirred for 15 min. Then, it is filtered over a glass suction filter D4 to remove the catalyst 2. The filter cake is washed with 3*45 mL heptane and 3*45 mL propylene carbonate. The residue is sucked to dryness and further dried in a stream of nitrogen for 3 days (moist weight: 42.76 g, dry weight: 35.15 g). The thus recycled bentonite catalyst 2 is again applied in example 2.24.2.

All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 68.80 g of crude all racemic alpha-tocopherol acetate (79.90 GC-area-%) is obtained as ocher-yellow, clear, viscous residue containing 8.34 GC-area % alpha-tocopherol. This corresponds to a yield of 78% (based on GC-area % over 2 steps).

Example 2.24.2

Preparation of all Racemic Alpha-Tocopherol 100.29 g (83.3 mL) propylene carbonate and 35.15 g catalyst 2 from example 2.24.1 are added and heated to 120-125° C. and stirred for 15 min. The suspension is then cooled to <90° C. and 22.92 g (150 mmol) trimethylhydroquinone (1.0 eq) is added. The mixture is then again heated to 120° C. Then, 46.75 g (55.59 mL) isophytol (154.5 mmol, 98% purity, 1.03 eq) is continuously added to the reaction mixture over a period of 2 h (temperature of the reaction mixture: 120-123° C.) while the water formed during the reaction is removed by distillation. After a further reaction time of 4 h at 123-124° C. the reaction mixture is stirred over the weekend at room temperature.

Preparation of all Racemic Alpha-Tocopherol Acetate

Towards the brown suspension obtained from the previous step 30.94 g (28.64 mL) acetic anhydride (300 mmol, 2 eq) are continuously added over a period of 10 min. Then, the reaction mixture is reactively distilled for 2 h (500 mbar, inner temperature 87-92° C., transition temperature 28-33° C., oil bath temperature 100° C.). Then, the reaction mixture is brought to room temperature and 45 mL of heptane is added and the reaction mixture is stirred for 15 min. Then, it is filtered over a glass suction filter D4 to remove the catalyst 2. The filter cake is washed with 3*45 mL heptane and 3*45 mL propylene carbonate. All mother liquors and washing liquors are collected and joined. The phases of the eluate are separated. The propylene carbonate phase is extracted with 4*65 mL heptane. The combined heptane phases are dried over sodium sulfate and the volatiles are removed under reduced pressure at 50° C./5 mbar plus 15 min oil pump vacuum: 71.79 g of crude all racemic alpha-tocopherol acetate (88.08 GC-area-%) is obtained as brown, clear, viscous residue containing 0.18 GC-area % alpha-tocopherol. This corresponds to a yield of 89% (based on GC-area % over 2 steps).

2.25 Recycling of the TMH Used in Excess in the Carbonate Solvent

The possibility to recycle the non-reacted, excess TMH together with the carbonate solvent applied in the Friedel-Crafts-alkylation and condensation reaction was evaluated. Two reactions were conducted in analogy to example 2.8, except that 225 mmol TMH were applied here instead of 625.5 mmol TMH (the amounts of the other reactants were adapted accordingly) and that the non-reacted excess TMH is recovered in the carbonate solvent after completion of the reaction and reused in the following identical reaction. In both reactions the obtained yields were identical (examples 2.25.1 and 2.25.2 below, 87% yield in each case). Thus, the non-reacted, excess TMH can be successfully recycled together with carbonate solvent.

Example 2.25.1

Preparation of all Racemic Alpha-Tocopherol 80.55 g (66.9 mL) propylene carbonate, 40.9 g (58.18 mL) n-octane (plus 60 mL octane in dean-stark-trap) and 0.22 g catalyst 2 (dried at 120° C., overnight, 50 mbar)/g TMH (7.5 g catalyst 2) are heated under a nitrogen gas stream to slight n-octane reflux (temperature of the reaction mixture: 120-125° C.) and stirred for 15 min under reflux.

The suspension is then cooled to <80° C. and 34.52 g (225 mmol) trimethylhydroquinone (1.5 eq) is added. The mixture is then again heated to 121° C. Then, 45.86 g (54.52 mL) isophytol (150 mmol, 97% purity, 1 eq) is continuously added to the reaction mixture over a period of 2 h (temperature of the reaction mixture: 120-125° C.) while the water formed during the reaction is removed by distillation. After a further reaction time of 4 h at 124-125° C., at room temperature overnight, and further 2 h at 125° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 64.58 g of crude alpha-tocopherol (93.1 GC-area-% and 87.24 GC-weight-%) is obtained as dark red, clear, viscous residue. This corresponds to a yield of 87%. Furthermore, 172.31 g of a red clear propylene carbonate phase containing 93.6 GC-area-%, 6.2 HPLC-weight-% of unreacted TMH is obtained. This corresponds to a recovery of 93% TMH (70 mmol of 75 mmol of TMH used in excess). 85.87 g of this propylene carbonate phase is recycled in 2.25.2.

|  | alpha-tocopherol | | TMH | |
| --- | --- | --- | --- | --- |
|  | GC area-% | GC weight-% | GC area-% | HPLC weight-% |
| Raw alpha-tocopherol | 93.1 | 87.24 | 0 | — |
| Propylene carbonate phase | 0.2 | — | 93.6 | 6.2 |

Example 2.25.2

Preparation of all Racemic Alpha-Tocopherol 85.87 g of propylene carbonate phase from 2.25.1 (containing 5.32 g, 34.96 mmol, 0.23 eq TMH), 40.9 g (58.18 mL) n-octane (plus 60 mL octane in dean-stark-trap) and 0.22 g catalyst 2 (dried at 120° C., overnight, 50 mbar)/g TMH (7.5 g catalyst 2) are heated under a nitrogen gas stream to slight n-octane reflux (temperature of the reaction mixture: 120-123° C.) and stirred for 15 min under reflux. The suspension is then cooled to <80° C. and 29.16 g (190.04 mmol) trimethylhydroquinone (1.23 eq; in total: 1.46 eq) is added. The mixture is then again heated to 120° C. Then, 47.2 g (56.12 mL) isophytol (154.4 mmol, 97% purity, 1 eq) is continuously added to the reaction mixture over a period of 2 h (temperature of the reaction mixture: 120-125° C.) while the water formed during the reaction is removed by distillation. After a further reaction time of 4 h at 124-125° C., at room temperature overnight, and further 2 h at 125° C. the reaction mixture is cooled to room temperature and filtered over a glass suction filter D4 loaded with celite to remove the catalyst 2. The filter cake is washed with 3*45 mL n-octane and 3*45 mL propylene carbonate. All mother liquors and washing liquors are collected and joined. The phases of the eluate are separated. The propylene carbonate phase is extracted with 4*65 mL n-octane. The combined n-octane phases are dried over sodium sulfate and the volatiles are removed under reduced pressure at 55° C./5 mbar plus 15 min oil pump vacuum: 65.70 g of crude alpha-tocopherol (92.9 GC-area-% and 87.71 GC-weight-%) is obtained as dark red, clear, viscous residue. This corresponds to a yield of 87%. Furthermore, 196.85 g of a red clear propylene carbonate phase containing 91.5 GC-area-%, 5.5 HPLC-weight-% of unreacted TMH is obtained. This corresponds to a recovery of >99% TMH (71 mmol of 71 mmol of TMH used in excess).

|  | alpha-tocopherol | | TMH | |
| --- | --- | --- | --- | --- |
|  | GC area-% | GC weight-% | GC area-% | HPLC weight-% |
| Raw alpha-tocopherol | 92.9 | 87.71 | 0 | — |
| Propylene carbonate phase | 0.2 | — | 91.5 | 5.5 |

The invention claimed is:
1. Process for preparing a compound of the general formula I

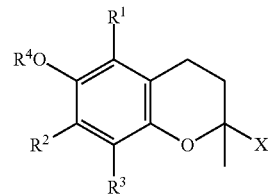

(I)

wherein
$R^1$, $R^2$ and $R^3$ independently of each other are selected from hydrogen and methyl,
$R^4$ is selected from hydrogen and $C_1$-$C_6$-alkanoyl, and
X is selected from $C_1$-$C_{20}$-alkyl and $C_2$-$C_{20}$-alkenyl,
comprising the following steps:
a) providing a quinone compound of the general formula II,

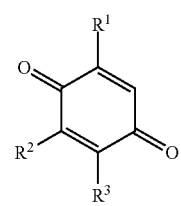

(II)

wherein $R^1$, $R^2$ and $R^3$ are as defined above,
b) catalytic hydrogenation of the quinone compound of formula II provided in step a) in the presence of hydrogen, a hydrogenation catalyst and in the presence of a carbonate solvent to obtain a hydroquinone compound of the general formula III,

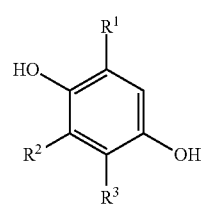

(III)

wherein $R^1$, $R^2$ and $R^3$ are as defined above, c) reacting the hydroquinone compound III provided in step b) with an unsaturated compound of the general formula IV.a or IV.b

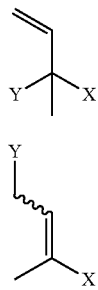

(IV.a)

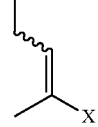

(IV.b)

wherein

X is as defined above,

Y is selected from OH, halogen, —O—$R^{11}$, —S—$R^{12}$ and —$SO_2$—$R^{12}$, $R^{11}$ is selected from $C_1$-$C_4$-alkyl, $C_1$-$C_4$-alkanoyl and trifluoroacetyl, and $R^{12}$ is selected from $C_1$-$C_6$-alkyl, trifluoromethyl and phenyl, where phenyl is unsubstituted or substituted with 1, 2, 3, 4 or 5 radicals selected from halogen and methyl, in the presence of a condensation catalyst, and d) in case $R^4$ is selected from $C_1$-$C_6$-alkanoyl, reacting the condensation product obtained in step c) with a $C_2$-$C_7$-carboxylic acid or with a $C_2$-$C_7$-carboxylic acid anhydride in the presence of an esterification catalyst, or reacting the condensation product obtained in step c) with an activated $C_2$-$C_7$-carboxylic acid in the presence of a base.

2. The process according to claim 1, where the carbonate solvent is selected from at least one organic carbonate and from mixtures, consisting of at least one organic carbonate and at least one apolar hydrocarbon solvent.

3. The process according to claim 2, where the content of the organic carbonate in the mixtures, consisting of at least one organic carbonate and at least one apolar hydrocarbon solvent, is in the range of from 50 to 99% by weight, based on the total weight of the mixtures.

4. The process according to claim 2, where the apolar hydrocarbon solvent is selected from the group consisting of linear and branched alkanes having 5 to 15 carbon atoms, cycloalkanes having 5 to 10 carbon atoms and aromatic hydrocarbons having 6 to 12 carbon atoms.

5. The process according to claim 2, where the organic carbonate is selected from cyclic and linear carbonates of the general formula V.a and V.b

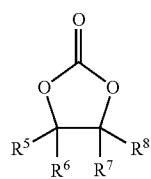

(V.a)

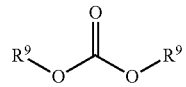

(V.b)

wherein $R^5$, $R^6$ and $R^7$ independently of each other are selected from hydrogen, methyl and ethyl, $R^8$ is selected from hydrogen, phenyl and $C_1$-$C_{15}$-alkyl, where $C_1$-$C_{15}$-alkyl is unsubstituted or substituted with 1, 2, or 3 radicals, selected from $C_1$-$C_3$-alkoxy, polyalkyleneoxide, phenyl and phenoxy, and $R^9$ independently of each other are selected from $C_1$-$C_4$-alkyl.

6. The process according to claim 2, where the organic carbonate is selected from the group consisting of ethylene carbonate, propylene carbonate, butylene carbonate, 2,3-propylene carbonate, isobutylene carbonate, dimethyl carbonate, diethyl carbonate and di-n-propyl carbonate.

7. The process according to claim 1, where in the compounds of the general formula I, II and III $R^1$, $R^2$ and $R^3$ are methyl and $R^4$ if present, is selected from hydrogen or ethanoyl.

8. The process according to claim 1, where X is methyl or has one of the following meanings X-1 to X-6

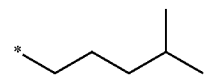

(X-1)

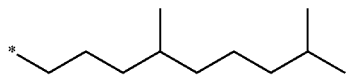

(X-2)

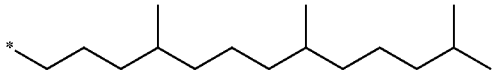

(X-3)

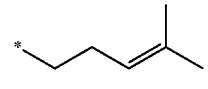

(X-4)

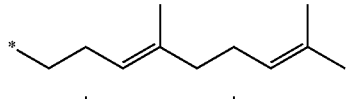

(X-5)

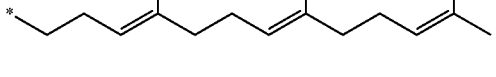

(X-6)

wherein * indicates the attachment point to the chromane ring.

9. The process according to claim 1, where step c) is carried out in a carbonate solvent.

10. The process according to claim 1, where the same carbonate solvent is used in each of the steps b) and c).

11. The process according to claim 1, where step c) is carried out in the carbonate solvent used in step b).

12. The process according to claim 1, where the reaction mixture obtained in step b) is used directly in the reaction in step c) after removal of the hydrogenation catalyst.

13. The process according to claim 1, where the condensation catalyst applied in step c) is selected from an acidic heterogeneous catalyst, and in particular from a treated bentonite catalyst.

14. The process according to claim 1, where step d) is carried out in a carbonate solvent.

15. The process according to claim 13, where steps b), c) and d) are carried out in the same carbonate solvent.

16. The process according to claim 13, where the esterification catalyst applied in step d) is selected from an acidic heterogeneous catalyst, and in particular from a treated bentonite catalyst.

17. The process according to claim 15, where steps c) and d) are performed in the presence of the same treated bentonite catalyst.

18. The process according to claim 16, where the reaction mixture obtained in step c) is used directly in the reaction in step d).

* * * * *